US006423752B1

(12) United States Patent
Walsh et al.

(10) Patent No.: US 6,423,752 B1
(45) Date of Patent: *Jul. 23, 2002

(54) INDANE DIMER COMPOUNDS WITH SMOOTH MUSCLE RELAXING AND/OR MAST CELL STABILIZING AND/OR ANTI-INFLAMMATORY ACTIVITY

(75) Inventors: John Walsh, Ballinrobe; Neil Frankish, Dublin; Helen Sheridan, Dublin; William Byrne, Dublin, all of (IE)

(73) Assignee: Venantius Limited, Dublin (IE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,903

(22) Filed: Jun. 8, 1998

Related U.S. Application Data

(63) Continuation of application No. PCT/IE96/00081, filed on Dec. 6, 1996.

(30) Foreign Application Priority Data

Dec. 6, 1995 (IE) .............................. 95 0922
Oct. 31, 1996 (IE) .............................. 96 0762

(51) Int. Cl.$^7$ .............................................. A01N 33/02

(52) U.S. Cl. ...................................... 514/656; 564/428

(58) Field of Search ................................. 564/307, 308, 564/428, 431; 568/48, 44, 53, 56, 58, 67, 665, 626

(56) References Cited

U.S. PATENT DOCUMENTS 3,314,854 A * 4/1967 Heider
3,668,258 A * 6/1972 Hageman ..................... 568/47

OTHER PUBLICATIONS

Monatshefte fur chemie by Riemschneider vol. 94 pp. 1131, 1132, 1963.*
J Amer Chem Soc by Whitmore et al 64 912–917, 1942.*
Ann Chim (Paris) 10 (4) Courtot pp. 256–258, 1925.*
J Amer Chem Soc by Suter vol. 60 pp. 1360–1365, 1938.*
Ann Chim (Paris) 10 (4) Courtot pp. 285–287, 1925.*
CA:76:58435 abs of Tetrahedron 27 (4) pp. 6159–6169 by Perjessy, 1971.*
Beilstein rn 3177504 paper of Chem Ber 52 pp. 110, 1919.*
CA:89146571 abs of Indian J Chem Sect B 16B(6) pp. 491–495 by Islam, 1978.*
CA:123:82705 abs of J Org Chem 60 (13) pp. 4067–4076 by Pincock, 1995.*
J Chem Society (London) by Haworth pp. 95–96, 1947.*
CA:123:246895 abs of WO9518617, Jul. 1995.*
Beilstein RN:266384 abs of J Gen Chem USSR (Engl. Translation) 30, p. 3601 by Lewchina et al, 1960.*
CA:98:125575 abs of J Med Chem 26(4) pp. 580–585 by Deana et al, 1983.*
Chemical Abstracts, vol. 117, No. 3, Jul. 20, 1992, Takenaka, "Attenuation of endothelin effects by a chloride . . . ".
AM. J. Physiol, vol. 262, No. 5, Pt. 2, 1992, pp. F799–F806.

* cited by examiner

*Primary Examiner*—Jean F. Vollano
(74) *Attorney, Agent, or Firm*—Jacobson Holman, PLLC

(57) ABSTRACT

Indane dimer compounds of general formula 5 or 6 are pharmaceutically useful, particularly to achieve smooth muscle relaxing activity and/or mast cell stabilizing activity and/or inflammatory activity. In formula 5 $R^1$, $R^2$ and $R^3$ to $R^{15}$ and in formula 6 $R^1$, $R^2$ and $R^4$ to $R^{15}$, are selected from one or more of the same of different of: H, halo, hydroxy, alkoxy, aryloxy, acetoxy, carboxy, alkyl carbonyl, hydro carbonyl, amino, amido, alkylamino, hydroxylamino, sulphonic acid groups, sulphoxide groups, sulphone groups, $C_1$–$C_{10}$ alkyl or $C_3$–$C_8$ cycloalkyl groups. In formulae 5 and 6, X is O or NR, and the R in NR may be hydrogen, acyl, alkyl or sulphonate groups. In formulae 5 and 6 any one or more of $R^1$, $^1R^1$; $R^1$, $^1R^2$; $R^9$, $^1R^9$; $R^{10}$, $^1R^{10}$ and $R^{14}$, $^1R^{10}$ may together represent oxo.

20 Claims, No Drawings

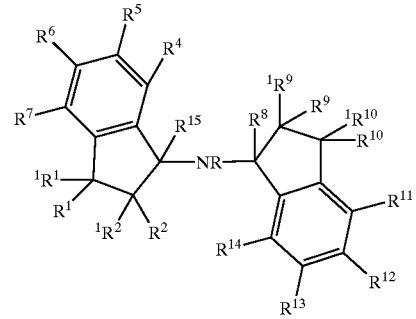

5

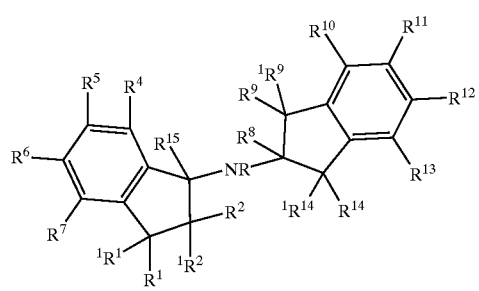

6

INDANE DIMER COMPOUNDS WITH SMOOTH MUSCLE RELAXING AND/OR MAST CELL STABILIZING AND/OR ANTI-INFLAMMATORY ACTIVITY

This application is a continuation of PCT/IE96/00081, filed Dec. 6, 1996.

The invention relates to indane compounds, processes for their production, compositions containing them and their pharmacological use.

According to the invention there is provided a compound of any of the formulae:

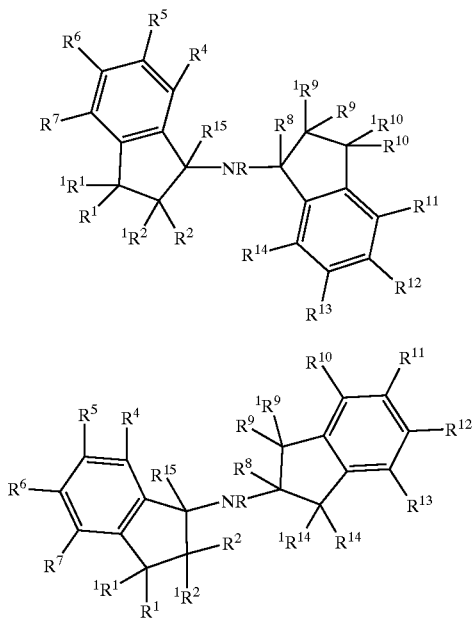

wherein
in Formulae 5 $R^1$ and $R^3$ to $R^{15}$
in Formula 6 $R^1$, $R^2$ and $R^4$ to $R^{15}$
are selected from one or more of the same or different of:
H, halo, hydroxy, alkoxy, aryloxy, acetoxy, carboxy, alkyl carbonyl, hydro carbonyl, amino, amido, alkylamino, hydroxylamino, amine oxide groups, azo groups, cyano, hydrazino groups, hydrazide groups, hydrazone groups, imide groups, iminoether groups, ureyl groups, oxime, nitro, nitrate, nitrite, nitroso groups, nitrile, heterocyclic groups containing one or more heteroatoms selected from N, O or S, aralkyl groups, mono and polybenzoid aryl groups, substituted aryl groups, thiol, thioureyl, phenylthiol groups, sulphonic acid groups, sulphoxide groups, sulphone groups, alkyl containing 1 to 10 carbon atoms or cycloalkyl groups containing 3 to 8 carbon atoms which may be saturated or unsaturated, substituted akyl or cycloalkyl groups which may be saturated or unsaturated
in Formulae 5, and 6 X is O, NR (wherein R is acyl, alkyl or sulphonate groups), S, SO or $SO_2$
in Formula 5 any one or more of $R^1$, $^1R^1$; $R^3$, $^1R^3$; $R^9$, $^1R^9$; and $R^{10}$, $^1R^{10}$ may together represent oxo,
in Formula 6 any of $R^1$, $^1R^1$; $R^2$, $^1R^1$; $R^9$, $^1R^9$; and $R^{14}$, $^1R^{14}$ may together represent oxo, and
a pharmacologically acceptable salts, esters, amides, solvates and isomers thereof.

In one embodiment of the invention the alkyl or cycloalkyl are substituted with one or more of the same or different of halo, oxo, hydroxy, alkoxy, aryloxy, acetoxy, carboxy, carbonyl, amino, amido, alkylamino, hydroxyamino, amine oxide groups, azo groups, cyano, hydrazino groups, hydrazide groups, hydrazone groups, imide groups, imino ether groups, ureyl groups, oxime, nitro, nitrate, nitrite, nitroso groups, nitrite, heterocyclic groups containing one or more heteroatoms selected from N, O or S, aralkyl groups, mono and polybenzoid aryl groups, substituted aryl groups, thiol, thioureyl, phenyl thiol groups, sulphonic acid groups, sulphoxide groups and sulphone groups.

In one embodiment of the invention the heterocyclic groups contain one or more heteroatoms selected from N, O or S.

In Formulae 5, and 6 $R^4$ to $R^7$ may be hydrogen. In Formula 5, $R^{11}$ to $R^{14}$ and in Formulae 6, $R^{10}$ to $R^{13}$ may also be hydrogen.

In Formula 5, and 6 preferred particularly because of pharmacological activity are those compounds in which X represents NR wherein R is acyl, alkyl or sulphonate groups.

Preferred particularly because of activity as anti-inflammatory agents are those compounds in which R represents acyl.

Preferred particularly because of activity as mast cell stabilising agents are those compounds in which R represents alkyl or sulphonate.

The invention relates to the compounds above for use particularly as smooth muscle relaxants and/or as mast cell stabilising agents and/or as anti-inflammatory agents.

The invention also relates to pharmaceutical compositions containing the compounds and to their use in methods of prophylaxis or treatment particularly to achieve smooth muscle relaxant activity and/or mast cell stabilising activity and/or anti-inflammatory activity.

The invention also relates to the compounds per se given in Appendix 2.

The invention also provides various processes for preparing the indane dimers as outlined in the claims. These processes are described in more detail below.

General Reaction Procedures

1. Coupling of 1-amino and 2-amino Indan Derivatives to 3-bromo-indanone Derivatives The general reaction procedure for this reaction is as follows: Either 1-amino indan or 2-amino indan was dissolved in dry DCM and to this an equivalent of 3-bromo indanone was added. The reaction solution was then cooled to 0° C. and triethyl amine was added as the tertiary base. The solution was allowed to stir at 0° C. for 3 hours. The product was purified by flash column chromatography.

2. N-Alkylation of the Products from Reaction Procedure No. 1

The 1 or 2-aminoindan dimer was dissolved in DCM and to this was added triethylamine as the tertiary base. The desired alkylation agent was then added and the solution was allowed to stir at room temperature for 3 hours. The reaction mixture was then passed through a flash silica column and the product was eluted.

3. N-sulfonylation of the Products from Reaction Procedure No. 1

1 or 2-aminoindan dimer was dissolved in DCM and to this was added p-toluenesulfonyl chloride and triethylamine. The solution was allowed to stir at 0° C. for 15 mins and then at room temperature for a further hour. Pyridine was then added to the reaction solution and the reaction was allowed to stir for a further 2 hours. The crude reaction mixture was passed through a flash silica column.

4. N-acylation of the Products from Reaction Procedure No. 1

1 or 2 aminoindan dimer was dissolved in DCM and to this was added triethylamine and acetic anhydride. To this stirring solution DMAP was added. The reaction was allowed to stir at room temperature for 3 hours. To the reaction mixture was added a 2M solution of aqueous HCl and the solvent was removed using toluene. To the crude material an aqueous solution of NaHCO$_3$ was added and the product was extracted into ether, the organic layers were combined and the solvent removed. The crude material was then passed through a flash silica column.

5. Sodium Borohydride Reduction of Dimers

This reduction is particularly applicable to the reduction of the ketone functional group of the compounds. The reduction procedure was as follows.

The required dimer was dissolved in ethanol and sodium borohydride was added to the reaction in small portions over 10 mins. The reaction was then stirred at room temperature for 3 hours. The reaction mixture was poured onto water (20 ml) and extracted into diethyl ether (3×20 ml). Flash column chromatography over silica gel afforded the product.

6. Cyanoborohydride Reduction of Diners

This reduction procedure is particularly applicable to the reduction of the ketone functional group of the compounds. The reduction is as follows.

The required dimer was dispersed in 1,2-dichloroethane at room temperature. To this solution was added solid zinc iodide and sodium cyanborohydride. The reaction was stirred at reflux for 20 hours. The product was added to water and extracted into ethyl acetate. Flash column chromatography (eluent: petroleum ether:ethyl acetate, 9:1) was used to isolate the pure product.

7. Hydrolysis of an Ester

The required ester was dissolved in a solution of 1.45 M NaOH in THF:MeOH:H$_2$O (6:3:2), which was then refluxed. After 20 minutes, TLC showed that the hydrolysis of the ester was complete. After cooling the reaction mixture, a saturated solution of aqueous ammonium chloride, aqueous HCl (2M) and ether was added. The organic layer was isolated and the aqueous layer was extracted with ether. The combined organic extracts were dried with Na$_2$SO$_4$ and filtered. Evaporation of the solvent, left the acid.

8. Oxime Synthesis

This procedure is particularly applicable for the synthesis of oxime derivatives of ketonic indane dimers which have hydrogens to the ketone. Generally the procedure was as follows.

The ketonic indanone dimer was dissolved in a solution of methanol:pyridine (4:1) and to this solution was then added hydroxylamine hydrochloride. Depending on the specific ketonic indan dimer, the reaction was carried out either at room temperature or at reflux conditions.

9. O-alkylation of the Oxime

This procedure is particularly applicable to O-alkylation of the oxime derivatives synthesised. Generally the procedure was as follows.

A solution of the oxime indane dimer was dissolved in ether:tert-butanol 3:1. Benzyl bromide was generally set as the alkylating reagent and it was added to the reaction mixture. Potassium tert-butoxide 1 eq. was added dropwise to this solution at room temperature. After workup using aqueous ammonium chloride and ether the desired oxime ether was isolated after chromatography.

10. Indan Ether Dimers

This procedure is particularly applicable for the self coupling of two 1-indanol molecules to give indan ether dimeric compounds with the loss of water.

The desired 1-indanol derivative was dissolved in DCM at 0° C. and an equivalent of methane sulfonyl chloride or methane sulfonic anhydride was added to the reaction mixture. N,N-diisopropylethyl amine was added dropwise as the tertiary base. The reaction mixture was left stirring for either at 0° C. or at room temperature, depending on the particular 1-indanol.

11. Acetylation of the Hydroxyl Indan-dimers

Generally the procedure was to dissolve the compound for acetylation in DCM and to use acetic anhydride as the acetylating reagent with triethylamine as tertiary base and DMAP as the acylation catalyst.

Synthesis of 5C3

Coupling Reaction

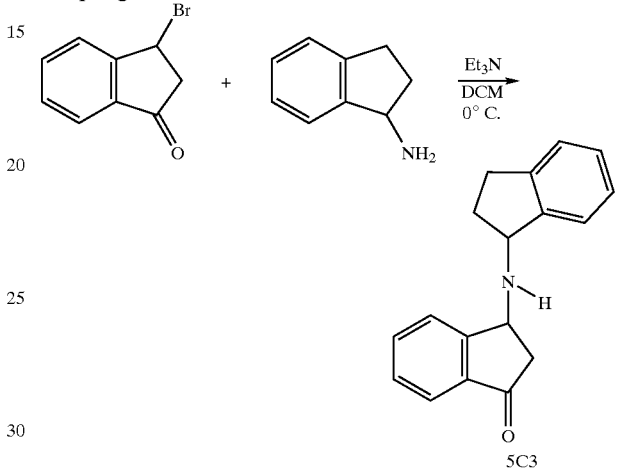

5C3

To a solution of 3-bromo-indan-1-one (200 mg, 0.952 mmol) and 1-aminoindan (130 mg, 0.952 mmol) in dry DCM (10 ml) at 0° C. was added triethylamine (0.19 g, 0.26 ml, 1.90 mmol). The solution was allowed to stir at 0° C. for 3 hours. The crude reaction mixture was passed through a plug of silica, eluting with petroleum ether:ethyl acetate (4:1). 5C3 was isolated as a white solid (150 mg, 60%).

$^1$H NMR (CDCl$_3$, 300 MHz) $\delta_H$ 1.77–1.89 (1H, m, CH of CHCH$_2$C$\underline{H}_2$), 2.43–2.53 (1H, m, CH of CHCH$_2$C$\underline{H}_2$), 2.58 (1H, dd, J=3.4 Hz & 18.5 Hz, CH of CHC$\underline{H}_2$), 2.79–2.89 (1H, m, CH of CHC$\underline{H}_2$CH$_2$), 2.99–3.04 (1H, m, CH of CHC$\underline{H}_2$CH$_2$), 3.09 (1H, dd, J=6.7 Hz & 18.7 Hz, CH of CHC$\underline{H}_2$), 4.43 (1H, t, J=6.7 Hz, C$\underline{H}$CH$_2$CH$_2$), 4.65 (1H, q, J=3.5 Hz & 6.7 Hz, C$\underline{H}$CH$_2$), 7.21–7.27 (3H, m, 3×Ar—$\underline{H}$), 7.41–7.47 (2H, m, 2×Ar—$\underline{H}$), 7.65 (1H, dt, J=1.2, 7.7 Hz, 1×Ar—$\underline{H}$), 7.75 (2H, 2 overlapping t, 2×Ar—$\underline{H}$).

$^{13}$C NMR (CDCl$_3$, 75.47 MHz) $\delta_C$ 30.4, 36.0, 46.8 (3×$\underline{C}$H$_2$), 52.2, 62.5 (2×$\underline{C}$H), 123.3, 124.1, 124.9, 126.0, 126.3, 127.6, 128.6, 134.8 (8×Ar—CH), 136.6, 143.4, 145.3, 156.6 (4×Ar—C), 204.6 (C=O).

Coupling of S-(+)-1-aminoindan to 3-bromoindanone to Give Two Diastereomers of 5C3 which are Called 5C3 Bottom S and 5C3 Top S Synthesis of 5C3 Bottom (S) and Top (S) Isomers Stereospecific Coupling Reaction

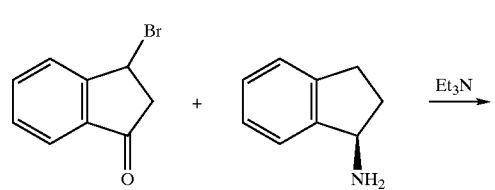

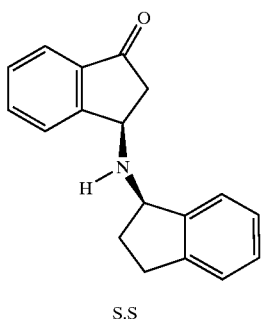
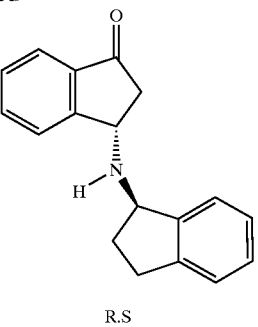

S.S            R.S 3-bromoindanone (780 mg, 3.73 mmol) was placed in a dry flask with DCM (10 ml). To this was added S(+)-1-aminoindane (500 mg, 3.78 mmol) and triethylamine (750 mg, 0.96 ml, 7.42 mmol). The solution was allowed to stir at 0° C. for 2 hours. The crude reaction mixture was passed through a plug of silica, eluting the products with petroleum ether:ethyl acetate (7:3). The top diastereomer was obtained after evaporation of the eluent and was further purified by washing the solid with petroleum ether. The bottom diastereomer fraction was found to be insoluble in ether and this was used as a method of purification. Combined yield was recorded as (660 mg, 68.9%).

BOTTOM (S) Diastereomer 5C3 Bottom S $^1$H NMR (CDCl$_3$, 300 MHz) $\delta_H$ 1.63 (1H, s, NH), 1.76–1.88 (1H, m, 1H of CHCH$_2$CH$_2$), 2.42–2.52 (1H, m, 1H of CHCH$_2$CH$_2$), 2.53 & 2.60 (1H, 2xd, J=3.5 Hz, H of CHCH$_2$CO), 2.78–2.88 (1H, q, J=7.7 Hz, H of CHCH$_2$CH$_2$), 2.98–3.04 (1H, m, H of CHCH$_2$CH$_2$), 3.06 & 3.11 (1H, 2xd, J=6.6 Hz, H of CHCH$_2$CO), 4.42 (1H, t, J=6.7 Hz, CHCH$_2$CH$_2$), 4.61 (1H, q, J=3.3 & 6.6 Hz, CHCH$_2$CO), 7.21–7.28 (3H, m, 3×Ar—H), 7.41–7.46 (2H, superimposed t, J=0.9 & 7.9 Hz, 2×Ar—H), 7.65 (1H, 2xt, J=0.9 & 7.9 Hz, 1×Ar—H), 7.72–7.82 (2H, m, 2×Ar—H).

$^{13}$C NMR (CDCl$_3$, 75.47 MHz) $\delta_C$ 30.3 (CH$_2$CH$_2$CHNH), 36.0 (CH$_2$CH$_2$CHNH), 46.7 (NHCHCH$_2$CO), 55.1 (NHCHCH$_2$CO), 62.4 (CH$_2$CH$_2$CHNH), 123.1, 124.0, 124.8, 126.0, 126.2, 127.5, 128.5, 134.7 (8×Ar—CH), 136.5, 143.3, 145.3, 156.5 (4×Ar—C), 204.5 (C=O).

TOP (S) Diastereomer 5C3 Top S $^1$H NMR (CDCl$_3$, 300 MHz) $\delta_H$ 1.70 (1H, s, NH), 1.94–2.00 (1H, q, J=7.1 z, H of CHCH$_2$CH$_2$), 2.51–2.58 (1H, m, 1H of CHCH$_2$CH), 2.61 & 2.67 (1H, dd, J=2.8, 18.4 Hz, H of CHCH$_2$CO), 2.83–2.93 (1H, q, J=7.7 Hz, H of CHCH$_2$CH$_2$), 3.03 (1H, d, J=6.6 Hz, H of CHCH$_2$CH$_2$), 3.10 (1H, d, J=6.4 Hz, H of CHCH$_2$CO), 4.39 (1H, t, J=6.6 Hz, CHCH$_2$CH$_2$), 4.64 (1H, t, J=2.8 Hz, CHCH$_2$CO), 7.19–7.31 (4H, m, 4×Ar—H), 7.44 (1H, t, J=7.4 Hz, 1×Ar—H), 7.58–7.69 (2H, m, 2×Ar—H), 7.75–7.82 (1H, d, 1×Ar—H).

$^{13}$C NMR (CDCl$_3$, 75.47 MHz) $\delta_C$ 30.4 (CH$_2$CH$_2$CHNH), 34.3 (CH$_2$CH$_2$CHNH), 45.8 (NHCHCH$_2$CO), 54.0 (NHCHCH$_2$CO), 61.6 (CH$_2$CH$_2$CHNH), 123.4, 123.9, 124.8, 125.8, 126.5, 127.7, 128.7, 134.9 (8×Ar—CH), 136.9, 143.5, 144.8, 156.2 (4×Ar—C), 204.7 (C=O).

Coupling of R-(+)-1-aminoindan to 3-bromoindanone to Give Two Diastereomers of 5C3 which are Called 5C3 Bottom R and 5C3 Top R
Synthesis of 5C3 Bottom R and Top R
5 1 Stereospecific Coupling Reaction

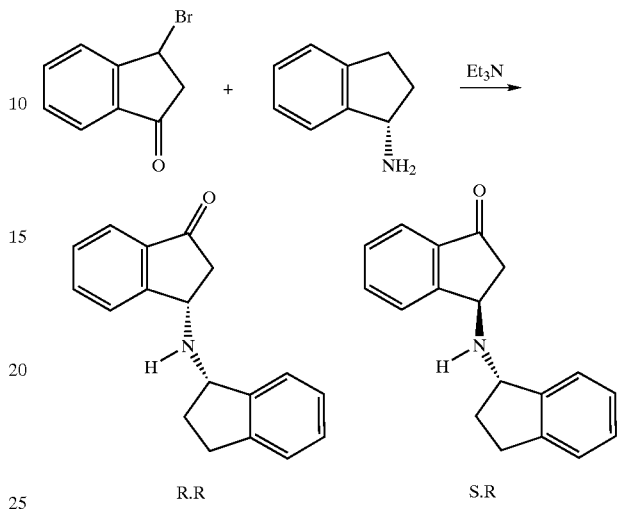

R.R            S.R 3-bromoindanone (780 mg, 3.73 mmol) was placed in a dry flask with DCM (10 ml). To this was added R(−)-1-aminoindane (500 mg, 3.73 mmol) and triethylamine (750 mg, 0.96 ml, 7.46 mmol). The solution allowed to stir at 0° C. for 2 hours. The crude reaction mixture was passed through a flash silica column, eluting the products with petroleum ether:ethyl acetate (7:3). The top diastereomer was obtained after evaporation of the eluent and was further purified by washing the solid with petroleum ether. The bottom diastereomer fraction was found to be insoluble in ether and this was used as a method of purification of the bottom spot. Combined yield for these compounds (680 mg, 68.9%).

Bottom (R) Diastereomer 5C3 Bottom R $^1$H NMR (CDCl$_3$, 300 MHz) $\delta_H$ 1.63 (1H, s, NH), 1.83–1.85 (1H, m, 1H of CHCH$_2$CH$_2$), 2.42–2.52 (1H, m, 1H of CHCH$_2$CH$_2$), 2.53 & 2.60 (1H, 2xd, J=3.5 Hz, H of CHCH$_2$CO), 2.78–2.88 (1H, q, J=7.7 Hz, H of CHCH$_2$CH$_2$), 2.98–3.04 (1H, m, H of CHCH$_2$CH$_2$), 3.06 & 3.11 (1H, 2xd, J=6.6 Hz, H of CHCH$_2$CO), 4.42 (1H, t, J=6.7 Hz, CHCH$_2$CH$_2$), 4.61 (1H, q, J=3.3 & 6.6 Hz, CHCH$_2$CO), 7.21–7.28 (3H, m, 3×Ar—H), 7.41–7.46 (2H, superimposed t, J=0.9 & 7.9 Hz, 2×Ar—H), 7.65 (1H, 2xt, J=0.9 & 7.9 Hz, 1×Ar—H), 7.72–7.72 (2H, m, 2×Ar—H).

$^{13}$C NMR (CDCl$_3$, 75.47 MHz) $\delta_C$ 30.3 (CH$_2$CH$_2$CHNH), 35.9 (CH$_2$CH$_2$CHNH), 46.6 (NHCHCH$_2$CO), 55.0 (NHCHCH$_2$CO), 62.4 (CH$_2$CH$_2$CHNH), 123.0, 123.9, 124.7, 125.9, 126.1, 127.4, 128.4, 134.6 (8×Ar—CH), 136.4, 143.2, 145.2, 156.4 (4×Ar—C), 204.4 (C=O).

Top (R) Diastereomer 5C3 Top R $^1$H NMR (CDCl$_3$, 300 MHz) $\delta_H$ 1.70 (1H, s, NH), 1.94–2.00 (1H, q, J=7.1 z, H of CHCH$_2$CH$_2$), 2.51–2.58 (1H, m, 1H of CHCH$_2$CH$_2$), 2.61 & 2.67 (1H, dd, J=2.8 Hz, H of CHCH$_2$CO) 2.83–2.93 (1H, q, J=7.7 Hz, H of CHCH$_2$CH$_2$), 3.03 (1H, d, J=6.6 Hz, H of CHCH$_2$CH$_2$), 3.10 (1H, d, J=6.4 Hz, H of CHCH$_2$CO), 4.39 (1H, t, J=6.6 Hz, CHCH$_2$CH$_2$), 4.64 (1H, t, J=2.8 Hz, CHCH$_2$CO), 7.19–7.31 (4H, m, 4×Ar—H), 7.44 (1H, t, J=7.4 Hz, 1×Ar—H), 7.58–7.69 (2H, m, 2×Ar—H), 7.75–7.82 (1H, d, J=7.5 Hz, 1×Ar—H).

$^{13}$C NMR (CDCl$_3$, 75.47 MHz) δ$_C$ 30.3 (CH$_2$CH$_2$CHNH), 34.2 (CH$_2$CH$_2$CHNH), 45.8 (NHCHCH$_2$CO), 53.9 (NHCHCH$_2$CO), 61.6 (CH$_2$CH$_2$CHNH), 123.3, 123.8, 124.7, 125.7, 126.4, 127.6, 128.6, 134.8 (8×Ar—CH), 136.8, 143.4, 144.8, 156.2 (4×Ar—C), 204.6 (C=O).

Synthesis of 5C4

Sodium Borohydride Reduction of 5C3

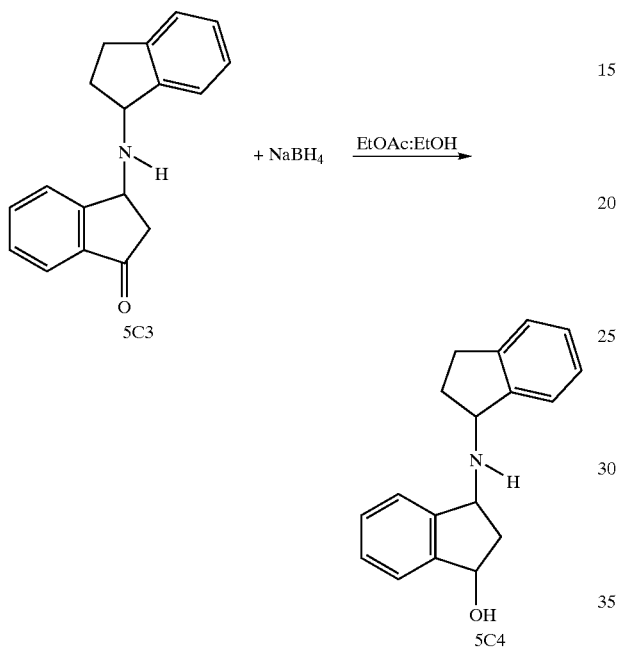

Dimer 5C3 (100 mg, 0.38 mmol) was dissolved in ethanol (4 ml) and ethyl acetate (8 ml). To this solution sodium borohydride (0.1 g, 2.63 mmol) was added to the reaction in small portions over 10 minutes. The reaction was stirred at room temperature for 3 hours. Evaporation of the solvent left a white solid and to this was added DCM. Filtration followed by evaporation left a mobile oil which was taken up in the minimum amount of DCM and passed through a plug of silica, eluting with petroleum ether (b.p. 40–60° C.):ethyl acetate, 98:2) afforded 5C4 as a mixture of diastereomers (25 mg, 25%).

$^1$H NMR (CDCl$_3$, 300 MHz) δ$_s$: 1.84–1.90 (1H, m, CH of CHCH$_2$CH$_2$) 1.93 (1H, t, J=3.7 Hz CH of CHCH$_2$CH$_2$) 2.06–2.37 (1H, m, CH of CHCH$_2$CH$_2$) 2.48–2.68 (2H, m, CH of NHCH$_2$) 2.86 (1H, q, J=8.5 Hz, CH of CHCH$_2$) 2.98–3.01 (1H, m, CH of CHCH$_2$CH$_2$) 4.63 (1H, t, J=5.9, C HCH$_2$CH$_2$) 5.02–5.31 (1H, 2×m, CH$_2$CHOH) 7.18–7.50 (8H, m, 8×Ar—H)

$^{13}$C NMR (CDCl$_3$, 75.47 MHz) δ$_C$ 30.3, 34.3, 45.0, (CH$_2$), 59.1, 61.5, (CHNH), 74.5, (CHOH), 124.0, 124.1, 124.2, 124.3, 124.6, 124.7, 124.8, 126.3, 126.4, 127.3, 127.4, 127.5, 128.0, 128.0, 128.1, 128.3, 128.4, 128.5, 128.6 (8×Ar—CH), 143.2, 143.2, 143.3, 143.3, 143.5, 143.5, 144.1, 144.5, 144.5, 144.6, 144.7, 144.8, 145.0, 145.3, 145.4, 145.6, 145.7 (4×Ar—C).

Synthesis of 5C5

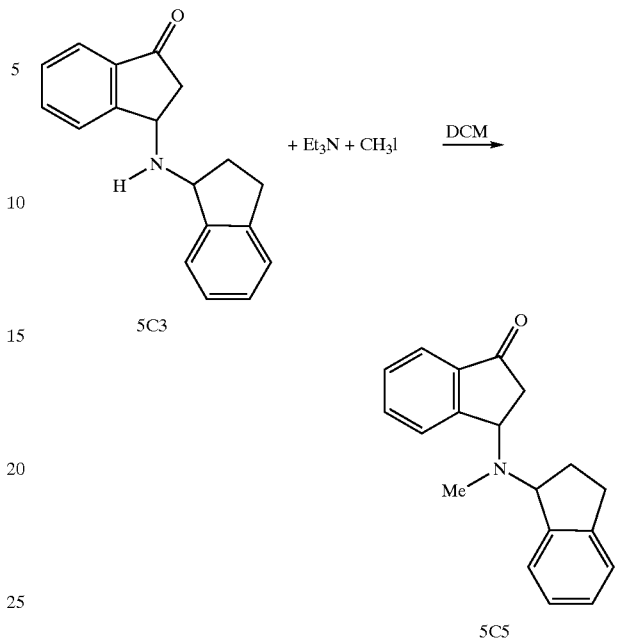

To a solution of dimer 5C3 (200 mng, 0.76 mmol) in DCM (5 ml) was added triethylamine (0.09 g, 0.13 ml, 0.91 mmol) and methyiodide (1.08 g, 0.48 ml, 7.61 mmol). The solution was allowed to stir at room temperature for 2 hours. The solvent was removed and the crude reaction mixture was passed through a plug of silica, eluting with petroleum ether:ethyl acetate (8:2) to yield dimer 5C5 as a yellow oil (0.80 g, 38%).

$^1$H; NMR (CDCl$_3$, 300 MHz) δ$_H$ 1.89 & 2.27 (3H, 2×s, CH$_3$), 1.98–2.19 (2H, m, CHCH$_2$CH$_2$), 2.55 & 2.69 (1H, dd J=6.9 Hz, CH of CHCH$_2$CO), 2.74–2.89 (2H, m, CH of CHCH$_2$CO & CH of CHCH$_2$CH$_2$), 2.91–3.05 (1H, m, CH of CHCH$_2$CH2), 4.34 & 4.63 (1H, 2×t, J=7.7 Hz, NCH$_3$C HCH$_2$CH$_2$), 4.55 & 4.77 (1H, 2×dd, J=6.9 Hz, CHCHCO), 7.20–7.29 (3H, m, 3×Ar—H), 7.44 (1H, m, 1×Ar—H), 7.52 ( 1H, m, 1×Ar—H), 7.67 (1H, d$_{ab}$q, J=1.2 Hz & 7.4 Hz, 1×Ar—H), 7.75 (1H, t, J=6.7 Hz, 1×Ar—H), 7.84 (1H, dt, J=0.9 Hz & 7.7 Hz, 1×Ar—H).

$^{13}$C NMR (CDCl$_3$, 75.47 MHz) δ$_C$ 26.5, 27.1 (CH$_2$), 30.4, 31.8 (CH$_2$), 37.9, 38.8 (CH$_2$), 27.9, 34.2, (CH$_3$), 58.0, 61.7 (CH), 66.9, 69.9 (CH), 122.7, 122.8, 124.4, 124.5, 124.7, 126.1, 126.2, 126.3, 126.3, 126.3, 127.3, 127.3, 128.3, 128.3, 134.7, 134.7 (8×Ar—CH), 136.8, 136.9, 142.9, 143.1, 143.7, 143.9, 156.0, 156.3 (4×Ar—C), 204.7, 204.7 (C=O).

Synthesis of 5C6

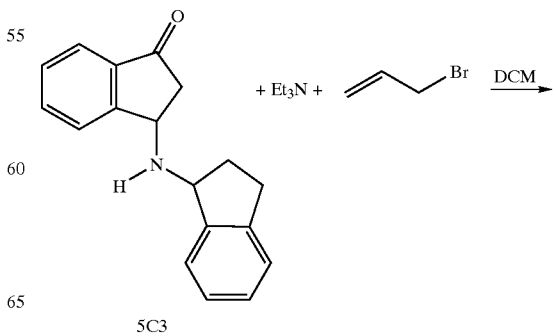

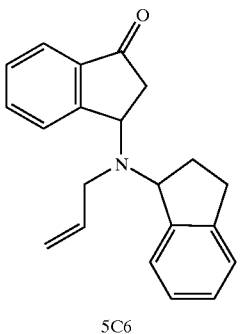

5C6

To a solution of dimer 5C3 (200 mg, 0.76 mmol) in DCM (5 ml) was added triethylamine (0.09 g, 0.13 ml, 0.91 mmol) and allyl bromide (0.90 g, 0.65 ml, 7.61 mmol). The solution was allowed to stir at room temperature for 2 hours. The solvent was removed and the crude reaction mixture was passed through a plug of silica, eluting with petroleum ether:ethyl acetate (8:2) to yield dimer 5C6 as a yellow oil (185 mg, 80%).

$^1$H NMR (CDCl$_3$, 300 MHz) $\delta_H$ 2.05 (2H, br m, CH$_2$), 2.47 (1H, dd, J=9.5 Hz, CH of CH$_2$), 2.72 (2H, m, CH$_2$CH=CH$_2$), 3.11 (3H, br m, CH of CH$_2$'s), 4.40, 4.50 (1H, 2xt, J=3.0 Hz, NCHCH$_2$CH$_2$), 4.65 (1H, m, CHCH$_2$CO), 4.97, 5.00, 5.10, 5.11, 5.14, 5.18, 5.27, 5.33 (2H, 8xbr m, CH$_2$CH=CH$_2$), 5.80 (1H, br m, CH$_2$CH=CH$_2$), 7.20 (3H, br m, 3xAr—H), 7.40, 7.50 (2H, 2xbr m, 2xAr—H), 7.64 (1H, br m, 1xAr—H), 7.74, 7.86 (2H, 2xbr m, 2xAr—H).

$^{13}$C NMR (CDCl$_3$, 75.47 MHz) $\delta_C$ 27.9, 29.6 (CH$_2$), 30.1, 30.3, 30.6 (CH$_2$), 40.1, 41.3 (CH$_2$), 49.5, 49.6 (CH$_2$), 55.8 57.0 (CH), 63.6, 64.6 (CH), 116.2, 116.8 (C=CH$_2$), 122.9, 123.0, 124.1, 124.6, 124.7, 124.9, 126.2, 126.2, 126.4, 126.6, 127.3, 127.6, 128.4 (8xAr—CH & 1xCH=CH$_2$), 134.5, 134.9, 137.0, 137.2, 137.4, 143.0, 143.3, 144.0, 144.5, 156.7 (4xAr—C), 204.9 (C=O).

Alkylation of 5C3 Bottom R Diastereomer with Allyl Bromide to Yield 5C6 Bottom S Diastereomer

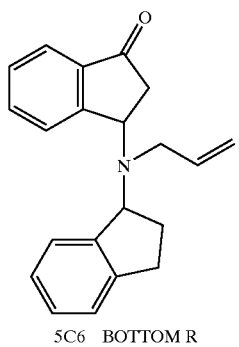

5C6 BOTTOM R

Dimer 5C3 Bottom R (200 mg, 0.76 mmol) was dissolved in DCM (2 ml) in a round bottomed flask and this was allowed to stir. To this solution was added triethylamine (0.09 g, 0.13 ml, 0.94 mmol) and allyl bromide (0.91 g, 0.65 ml, 7.38 mmol). The reaction was allowed to stir at room temperature for 8 hours. The crude reaction mixture was passed through a plug of flash silica, eluting with petroleum ether:ethyl acetate 7:3. On evaporation of the solvent a white solid 5C6 Bottom R was obtained (193 mg, 83.5%).

$^1$H NMR (CDCl$_3$, 300 MHz) $\delta_H$ 1.95–2.15 (2H, br m, CHCH$_2$CH$_2$), 2.54 (2H, 2xab q, J=18.9 & 16.9 Hz, CHCH$_2$), 2.74 & 2.94 (2H, m CHCH$_2$CH$_2$), 3.10 & 3.23 (2H, 2xab q, J=14.7, 16.0, 1.5 & 1.3 Hz, CH$_2$CHCH$_2$), 4.50 (1H, t, J=7.2 Hz, CHCH$_2$CH$_2$), 4.66 (1H, q, J=6.6 Hz, CHCH$_2$CO), 4.97 & 5.18 (1H, 2xdd, J=1.7 & 59.3, CH of CH$_2$CH=CH$_2$), 5.01 & 5.11 (1H, 2xdd, J=1.5 & 32.0 Hz, CH of CH$_2$CH=CH$_2$), 5.73 (1H, m, CH$_2$CHCH$_2$), 7.20 (3H, m, 3xAr—H), 7.39 (2H, m, 2xAr—H), 7.62 (1H, dt, J=1.32 & 7.26 Hz, 1xAr—H), 7.74 (2H, m, 2xAr—H).

$^{13}$C NMR (CDCl$_3$, 75.47 MHz) $\delta_C$ 30.1, 30.5, 41.3, 49.4, 116.1 (5xCH$_2$), 57.1, 64.6 (2xCH), 122.9, 124.8, 124.8, 126.2, 126.6, 127.5, 128.3, 134.4, 137.4 (8xAr—CH & 1xCH=CH$_2$), 137.1, 143.3, 144.0, 156.6 (4xAr—C), 204.7 (C=O).

Alkylation of 5C3 Bottom S Diastereomer with Allyl Bromide to Yield 5C6 Bottom S

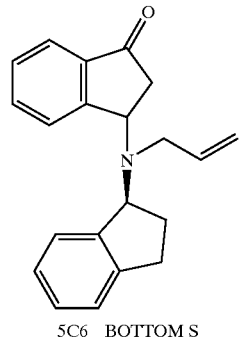

5C6 BOTTOM S

5C3 Bottom S (200 mg, 0.76 mmol) was dissolved in DCM (2 ml) in a round bottomed flask and this was allowed to stir. To this was added triethylamine (0.09 g, 0.13 ml, 0.94 mmol) and allyl bromide (0.91 g, 0.65 ml, 7.36 mmol). The reaction was allowed to stir at room temperature for 8 hours. The crude reaction mixture was passed through a plug of flash silica, eluting with petroleum ether:ethyl acetate 7:3. On evaporation of the solvent a white solid 5C6 Bottom S was obtained as a yellow solid (205 mg, 88.7%).

$^1$H NMR (CDCl$_3$, 300 MHz) $\delta_H$ 1.95–2.15 (2H, br m, CHCH$_2$CH$_2$), 2.54 (2H, 2xab q, J=18.9 & 16.9 Hz, CHCH$_2$), 2.74 & 2.94 (2H, m, CHCH$_2$CH$_2$), 3.11 & 3.25 (2H, 2xab q, J=14.5 & 14.7 Hz, CH$_2$CHCH$_2$), 4.51 (1H, t, J=7.2 Hz, CHCH$_2$CH$_2$), 4.67 (1H, m, CHCH$_2$CO), 4.99 & 5.15 (2H, 2xdd, J=9.9 & 17.1 Hz,CH$_2$CH=CH$_2$), 5.73 (1H, m, CH$_2$CHCH$_2$), 7.20 (3H, m, 3xAr—H), 7.41 (2H, m, 2xAr—H), 7.63 (1H, t, J=7.2 Hz, 1xAr—H), 7.74 (2H, m, 2xAr—H).

$^{13}$C NMR (CDCl$_3$, 75.47 MHz) $\delta_C$ 30.1, 30.5, 41.2, 49.4, 116.1 (5xCH$_2$), 57.0, 64.6 (2xCH), 122.9, 124.8, 124.8, 126.2, a126.5, 127.5, 128.3, 134.4, 137.4 (8xAR—CH & 1xCH=CH$_2$), 137.1, 143.2, 143.9, 156.6 (4xAr—C), 204.7 (C=O).

Alkylation of 5C3 Top R Diastereomer with Allyl Bromide to Yield 5C6 Top R

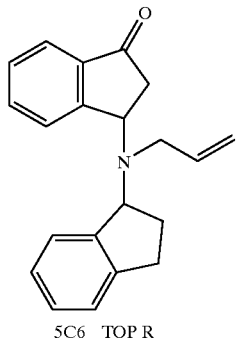

5C6 TOP R

Dimer 5C3 Top R (200 mg, 0.76 mmol) was dissolved in DCM (2 ml) in a round bottomed flask and this was allowed to stir. To this was added triethylamine (0.09 g, 0.13 ml, 0.94 mmol) and allyl bromide (0.91 g, 0.65 ml, 7.35 mmol). The reaction was allowed to stir at room temperature for 8 hours. The crude reaction mixture was passed through a plug of flash silica, eluting with petroleum ether:ethyl acetate 7:3. On evaporation of the solvent a white solid 5C6 Top R was obtained (189 mg 81.8%).

$^1$H NMR (CDCl$_3$, 300 MHz) $\delta_H$ 1.87–2.16 (2H, br m, CHC$\underline{H}_2$CH$_2$), 2.72 (2H, m, CHC$\underline{H}_2$), 2.72 (1H, m, CH of CHCH$_2$C$\underline{H}_2$), 2.93 (1H, m, CH of CHCH$_2$C$\underline{H}_2$), 2.95–3.15 (2H, m, C$\underline{H}_2$CH=CH$_2$), 4.41 (1H, t, J=7.7 Hz, C$\underline{H}$CH$_2$CH$_2$), 4.64 (1H, t, J=5.0 Hz, C$\underline{H}$CH$_2$CO), 5.13–5.29 (2H, 2×dd, J=10.1 & 17.1 Hz, CH$_2$CH=C$\underline{H}_2$), 5.85 (1H, m, CH$_2$C$\underline{H}$CH$_2$), 7.23 (3H, m, 3×Ar—$\underline{H}$), 7.42 (1H, t, J=7.3 Hz, 1×Ar—$\underline{H}$), 7.52 (1H, d, J=7.0 Hz, 1×Ar—$\underline{H}$), 7.66 (1H, t, J=7.3 Hz, 1×Ar—$\underline{H}$), 7.73 (1H, d, J=7.4 Hz, 1×Ar—$\underline{H}$), 7.86 (1H, d, J=7.4 Hz, 1×Ar—$\underline{H}$).

$^{13}$C NMR (CDCl$_3$, 75.47 MHz) $\delta_C$ 27.9, 30.3, 40.1, 49.6, 116.8 (5×$\underline{C}$H$_2$), 55.9, 63.7 (2×$\underline{C}$H), 122.9, 124.2, 124.5, 126.2, 126.4, 127.4, 28.4, 134.9, 137.0 (8×Ar—$\underline{C}$H & 1×CH=CH$_2$), 137.3, 143.0, 144.5, 156.7 (4×Ar—$\underline{C}$), 204.8 ($\underline{C}$=O).

Alkylation of 5C3 Top S Diastereomer with Allyl Bromide to Yield 5C6 Top S Diastereomer

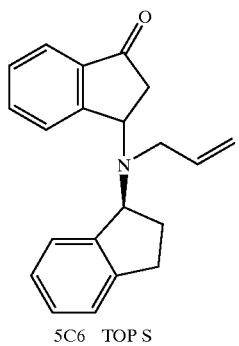

5C6 TOP S

Dimer 5C6 Top S (200 mg, 0.76 mmol) was dissolved in DCM (2 ml) in a round bottomed flask and this was allowed to stir. To this was added triethylamine (0.9 g, 0.13 ml, 0.94 mmol) and allyl bromide (0.91 g, 0.65 ml, 7.35 mmol). The reaction was allowed to stir at room temperature for 8 hours. The crude reaction mixture was passed through a plug of flash silica, eluting with petroleum ether:ethyl acetate 7:3. On evaporation of the solvent a white solid 5C6 Top S was obtained (197 mg, 85.3%).

$^1$H NMR (CDCl$_3$, 300 MHz) $\delta$1.91–2.15 (2H, br m, CHC$\underline{H}_2$CH$_2$), 2.72 (2H, m, CHC$\underline{H}_2$), 2.72 (1H, m, CH of CHCH$_2$C$\underline{H}_2$), 2.93 (1H, m, CH of CHCH$_2$C$\underline{H}_2$), 2.95–3.15 (2H, m, C$\underline{H}_2$CH=CH$_2$), 4.41 (1H, t, J=7.7 Hz, C$\underline{H}$CH$_2$CH$_2$), 4.64 (1H, t, J=5.0 Hz, C$\underline{H}$CH$_2$CO), 5.13–5.29 (2H, 2×dd, J=9.9 & 17.1 Hz, CH$_2$CH=C$\underline{H}_2$), 5.84 (1H, m, CH$_2$C$\underline{H}$CH$_2$), 7.19–7.26 (3H, br m, 3×Ar—H), 7.41 (1H, t, J=7.2 Hz, 1×Ar—H) 7.73 (1H, d, J=6.8 Hz, 1×Ar—H), 7.73 (1H, d, J=6.8 Hz, 1×Ar—H), 7.86 (1H d, J=7.6 Hz, 1×Ar—H).

$^{13}$C NMR (CDCl$_3$, 75.47 MHz) $\delta_C$ 27.9, 30.2, 40.1, 49.6, 116.7 (5×MHz), 55.8, 63.6 (2×$\underline{C}$H), 122.8, 124.1, 124.5, 126.1, 126.4, 127.3, 128.4, 134.8, 137.0 (8×Ar—$\underline{C}$H & 1×CH=CH$_2$), 137.2, 143.0, 144.4, 156.7 (4×Ar—$\underline{C}$), 204.7 (C=O).

Synthesis of 5C7

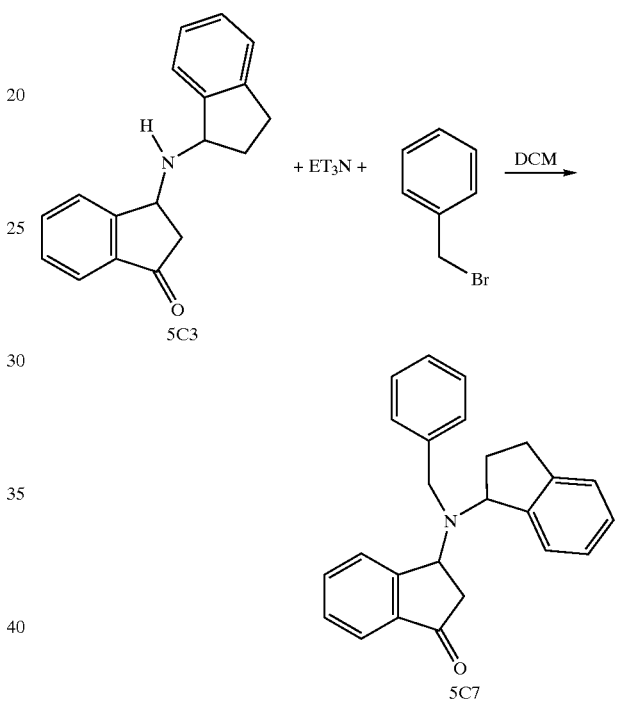

To a solution of dimer 5C3 (200 mg, 0.76 mmol) in DCM (5 ml) was added triethylamine (0.09 g, 0.13 ml, 0.91 mmol) and benzyl bromide (1.30 g, 0.90 ml, 7.61 mmol). The solution was allowed to stir at room temperature for 2 hours. The solvent was removed and the crude reaction mixture was passed through a plug of silica, eluting with petroleum ether:ethyl acetate (8:2) to yield 5C7 as a yellow oil (175 mg, 76%).

$^1$H NMR (CDCl$_3$, 300 MHz) $\delta_H$ 2.45, 2.76 (1H, 2×dd, J=7.1 Hz & 19.3 Hz, CH of COC$\underline{H}_2$CH), 2.63, 2.89 (1H, 2×dd, J=3.7 Hz & 19.3 Hz, CH of COC$\underline{H}_2$CH), 2.10, 2.78, 2.95 (4H, 3×br m, 2×C$\underline{H}_2$), 3.60 (1H, ab q, J=12.8 Hz & 17.9 Hz, H of PhC$\underline{H}_2$), 3.75 (1H, ab q, J=14.4 Hz & 52.8 Hz, CH of PhC$\underline{H}_2$) pair of diastereomers, 4.37, 4.42 (1H, 2×t, J=8.2 Hz & 7.3 Hz, NC$\underline{H}$CH$_2$CH$_2$), 4.58, 4.64 (1H, 2×dd, J=7.0 Hz & 4.0 Hz, 3.8 Hz, 7.0 Hz, NC$\underline{H}$CH$_2$CO), 7.35, 7.65 (12H, 2×br m, 12×Ar—$\underline{H}$), 7.83 & 7.98 (1H, 2×dd J=0.9 & 7.7 Hz, 1×Ar—$\underline{H}$).

$_{13}$C NMR (CDCl$_3$, 75.47 MHz) $\delta_C$ 27.2 (29.6), 30.3 (30.6), 39.5 (41.3), 50.6 (50.7), (4×$\underline{C}$H$_2$), 55.6 (56.1), 63.4 (63.2), (2×$\underline{C}$H), 122.8, 124.0, 124.5, 126.2, 126.3, 126.3, 126.8, 128.0, 128.0, 128.2, 128.2, 128.4, 134.7 (13×Ar—$\underline{C}$H), 137.2 (137.2), 139.6 (139.3), 143.4 (143.1), 144.2 (143.6), 156.5 (156.2), (5×Ar—$\underline{C}$), 204.6 (204.8), (C=O).

Synthesis of 5C8

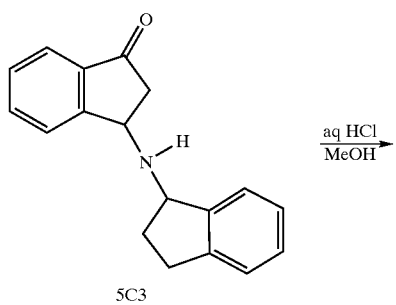

5C3 (200 mg, 0.76 mmol) was dissolved in methanol and to this was added a 2M aqueous HCl (5 ml). Toluene was then added and the solvent evaporated to dryness to afford a yellow solid. The solid was then dissolved in water and ethyl acetate was added to remove any organic impurities which were present. The water phase was extracted and was evaporated to dryness. The solid was then dissolved in the minimum amount of methanol and ethyl acetate was added. The product was then allowed to crystallise out. 5C8 was then afforded as a white powder (205 mg, 90.31%).

Synthesis of 5C9

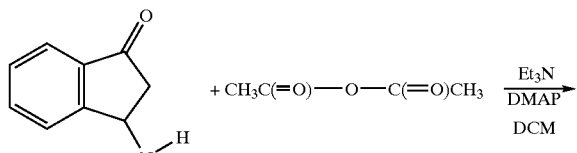

5C3 (200 mg, 0.76 mmol) was dissolved in DCM (5 ml) and to this was added triethylamine (1.54 g, 2.11 ml, 15.2 mmol) and acetic anhydride (1.55 g, 1.43 ml, 15.2 mmol). Then to this stirring solution DMAP (460 mg, 0.38 mmol) was added. The reaction mixture was allowed to stir at room temperature for 3 hours. To the reaction solution was added 2M aqueous HCl (5 ml) and 10 ml DCM. The organic layer was obtained and washed with water. To the organic was added to a 10% solution of NaHCO$_3$ (30 ml). The organic phase was collected and the aqueous layer was washed with DCM. All the organic layers were combined and dried over Na$_2$SO$_4$. The crude reaction was then passed through a plug of flash silica, eluting with petroleum ether 100% and grading to petroleum ether:ethyl acetate 1:4. The product 5C9 was obtained as a brownish solid (145 mg, 62.7%).

Synthesis of 5C10

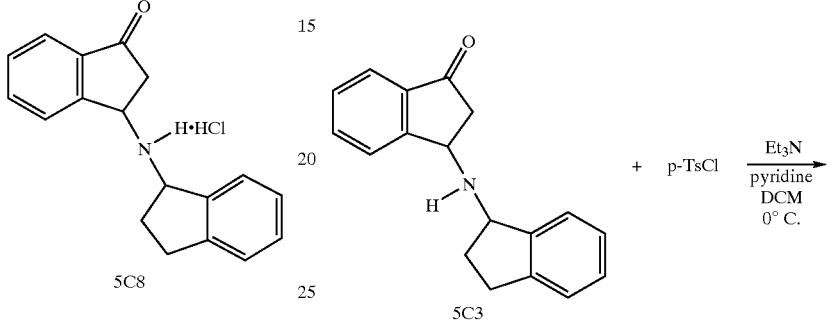

To a stirring solution of 5C3 (200 mg, 0.76 mmol) and p-toluenesulfonyl chloride (1.45 g, 7.60 mmol) in DCM (10 ml) was added triethylamine (0.09 g, 0.13 ml, 0.91 mmol). The solution was allowed to stir at 0° C. for 15 mins. The solution was allowed to stir at room temperature for a further hour then to this solution was added pyridine (0.26 ml) and the reaction was allowed to stir for a further 2 hours. The crude reaction mixture was passed through a flash silica column, eluting with petroleum ether:ethyl acetate 1:4. 5C10 was isolated as a yellow solid (284 mg, 89.3%).

Synthesis of 5C11

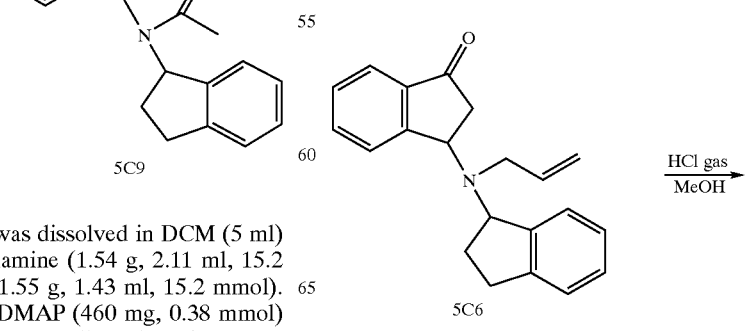

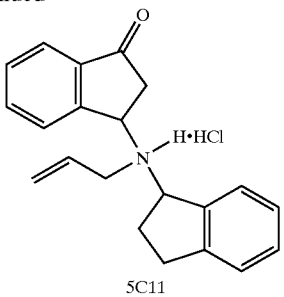

5C11

Compound 5C6 (100 mg) was dissolved in dry methanol (5 ml), dry HCl gas was bubbled through the solution for 5 mins. The methanol was then evaporated off and a white solid remained. The solid was then partioned between water and ether. The aqueous layers were combined and evaporated to dryness. The white solid 5C11 which remained was dried on the vac line (97%).

Synthesis of 5C12

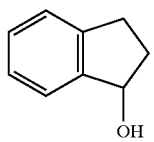

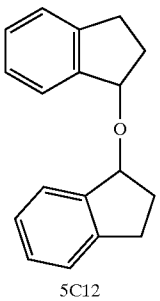

5C12

To a solution of 1-indanol 90.25 g, 1.87 mmol) in DCM (15 Ml) at 0° C. was added methane sulphonic anhydride (0.325 g, 1.87 mmol) and diisopropyethylamine (0.24 g, 1.87 mmol). The solution was left stirring at 0° C. for 5 hrs. The solvent was then evaporated to leave a mobile oil. The oil was then passed through a plug of silica. Evaporation of the relevant eluent gave a compound as a mobile oil which slowly crystallised overnight to give white crystals (0.20 g).

$^1$H NMR (CDCl$_3$, 300 MHz) σ$_H$ 2.21 (2H, m, C$\underline{H}_2$), 2.53 (2H, m, C$\underline{H}_2$), 2.92 (2H, m, C$\underline{H}_2$), 3.21 (2H, m, C$\underline{H}_2$), 5.28 (2H, br m, CH$_2$C$\underline{H}$OC$\underline{H}$CH$_2$), 7.32 (6H, br m, 6×Ar—$\underline{H}$), 7.51 (1H d, J=6.8 Hz, 1×Ar—$\underline{H}$), 7.55 (1H, d, J=7.0 Hz, 1×Ar—$\underline{H}$).

$^{13}$C NMR (CDCl$_3$, 75.47 MHz) σ$_C$ 29.9, 29.9, 32.2, 33.8 ($\underline{C}$H$_2$), 81.6, 82.2 (CH$_2\underline{C}$HO$\underline{C}$HCH$_2$), 124.6, 124.6, 124.7, 124.9, 126.2, 126.3, 127.9, 126.0 (8×Ar—H), 143.3, 143.3 (2×Ar—C), 143.5, 143.6 (2×Ar—C).

Synthesis of 6C4

Coupling reaction

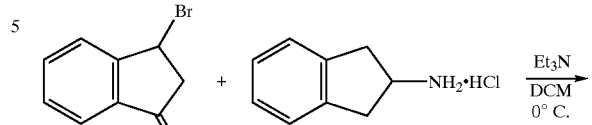

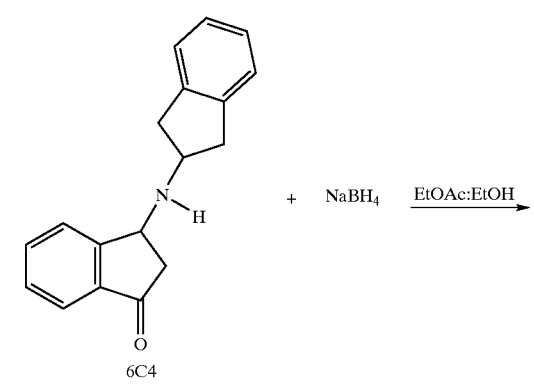

6C4

To a solution of 3-bromo-indan-1-one (200 mg, 0.952 mmol) and 2-aminoindan hydrochloride (160 mg, 0.952 mmol) in dry DCM (10 ml) at 0° C. was added triethylamine (0.19 g, 0.26 ml, 1.90 mmol). The solution was allowed to stir at 0° C. for 3 hours. The crude reaction mixture was passed through a plug of silica, eluting with petroleum ether:ethyl acetate (4:1). Salt formation 6C4 was isolated as a brown solid (150 mg, 60%).

$^1$H NMR (CDCl$_3$, 300 MHz) δ$_S$ 2.54 (1H, dd, J=3.2 Hz & 18.7 Hz, CH of CHC$\underline{H}_2$CO), 2.81 (1H, dd, J=6.8 Hz & 45.1 Hz, CH of CHC$\underline{H}_2$), 2.86 (1H, dd, J=6.9 Hz & 14.1 Hz, CH of CHC$\underline{H}_2$), 3.0 (1H, dd, J=6.7 Hz & 18.5 Hz, CH of CHC$\underline{H}_2$CO), 3.18 (1H, dd, J=6.9 Hz & 19.1 Hz, CH of CHC$\underline{H}_2$), 3.22 (1H dd, J=6.9 Hz & 19.3 Hz, CH of CHC$\underline{H}_2$), 3.81 (1H, quin, J=7.0 Hz, C$\underline{H}$CH$_2$), 4.51 (1H, q, J=3.1 Hz & 6.7 Hz, C$\underline{H}$CH$_2$CO), 7.14–7.29 (4H, m, 4×Ar—$\underline{H}$), 7.42–7.45 (1H, m, 1×Ar—$\underline{H}$), 7.59–7.75 (3H, m, 3×Ar—$\underline{H}$).

$^{13}$C NMR (CDCl$_3$, 75.47 MHz) δ$_C$ 39.5, 40.1, 45.0 (3× $\underline{C}$H$_2$), 54.1, 57.8 (2×$\underline{C}$H), 122.7, 124.0, 124.1, 125.4, 125.9, 125.9, 128.1, 134.2 (8×Ar—$\underline{C}$H), 136.1, 140.7, 140.9, 155.5 (4×Ar—$\underline{C}$), 203.9 ($\underline{C}$=O).

Synthesis of 6C5

Sodium borohydride reduction of 6C4

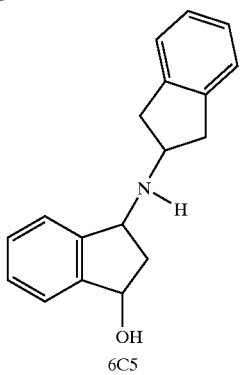

6C5

Dimer 6C4 (100 mg, 0.38 mmol) was dissolved in ethanol (4 ml) and ethyl acetate (8 ml). To this sodium borohydride (0.1 g, 2.63 mmol) was added to the reaction in small portions over 10 minutes. The reaction was stirred at room temperature for 3 hours. Evaporation of the solvent left a white solid and to this was added DCM. Filtration followed by evaporation left a mobile oil, which was then taken up in the minimum amount of DCM and passed through a plug of silica, eluting with petroleum ether (b.p. 40–60° C.):ethyl acetate, 98:2) afforded dimer 6C5 (39 mg, 39%).

$^1$H NMR (CDCl$_3$, 300 MHz) δ$_H$ 1.90 & 1.94 (1H, 2×t, J=3.5 Hz, CH of C$\underline{H}_2$CHOH), 2.55 & 2.59 (1H, 2×t, J=5.9 Hz, CH of C$\underline{H}_2$CHOH), 2.77–2.87 (2H, m, CHC$\underline{H}_2$), 3.18–3.29 (2H, m, CHC$\underline{H}_2$), 3.78–3.85 (1H, quin, J=6.7 Hz, C$\underline{H}$CH$_2$), 4.25 (1H, q, J=3.5 Hz & 5.7 Hz, C$\underline{H}$CH$_2$CHOH), 5.03 (1H q, J=3.4 Hz & 6.0 Hz, CH$_2$C$\underline{H}$OH), 7.15–7.26 (4H, m, 4×Ar—$\underline{H}$), 7.29–7.38 (3H, m, 3×Ar—$\underline{H}$), 7.47–7.49 (1H, m, 1×Ar—$\underline{H}$).

Synthesis of 6C6

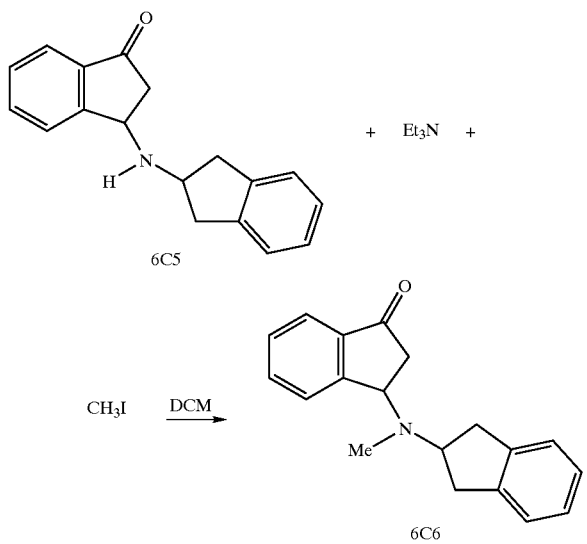

To a solution of dimer 6C5 (200 mg, 0.76 mmol) in DCM (5 ml) was added triethylamine (0.09 g, 0.13 ml, 0.91 mmol) and methyl iodide (1.08 g, 0.48 ml, 7.61 mmol). The solution was allowed to stir at room temperature for 2 hours. The solvent was removed and the crude reaction mixture was passed through a flash silica column, eluting with petroleum ether:ethyl acetate (8:2) to yield dimer 6C6 as a yellow oil (0.80 g, 38%).

$^1$H NMR (CDCl$_3$, 300 MHz) δ$_H$ 2.03 (3H, s, NC$\underline{H}_3$), 2.57 (1H, dd, J=7.0 Hz & 18.9 Hz, CH of CHC$\underline{H}_2$), 2.77 (1H, dd, J=3.8 Hz, & 18.9 Hz, CH of CHC$\underline{H}_2$), 2.93–3.17 (4H, m, 2×C$\underline{H}_2$), 3.46–3.57 (1H, quin, C$\underline{H}$CH$_2$), 4.78 (1H, q, J=3.5 Hz, C$\underline{H}$CH$_2$), 7.13–7.21 (4H, m, 4×Ar—$\underline{H}$), 7.43 (1H, t, J=7.0 Hz, 1×Ar—$\underline{H}$), 7.61 (1H, dt, J=1.0 Hz & 7.8 Hz, 1×Ar—$\underline{H}$), 7.72 (2H, t, J=6.0 Hz, 2×Ar—$\underline{H}$).

$^{13}$C NMR (CDCl$_3$, 75.47 MHz) δ$_C$ 33.1 ($\underline{C}$H$_3$), 35.8, 37.7, 38.0 (3×$\underline{C}$H$_2$), 59.6, 65.1 (2×$\underline{C}$H), 123.0, 124.3, 124.4, 126.3, 126.4, 126.4, 129.0, 134.7 (8×Ar—$\underline{C}$H), 137.2, 141.2, 141.4, 155.3 (4×Ar—$\underline{C}$), 205.0 ($\underline{C}$=O).

Synthesis of 6C7

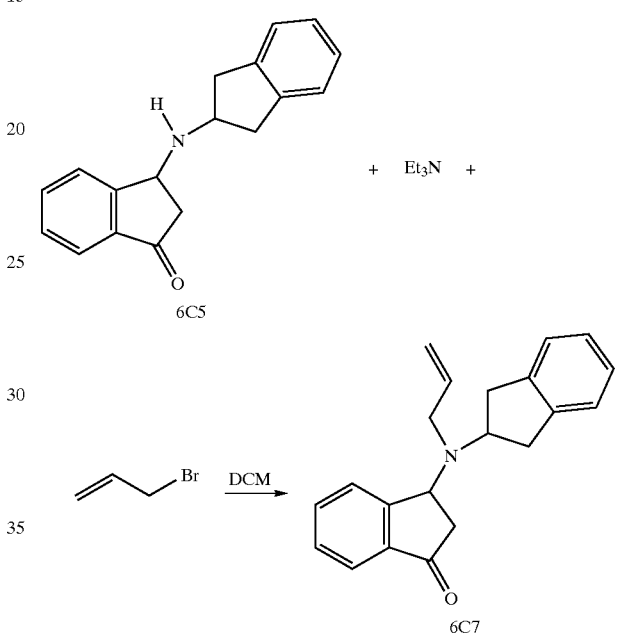

To a solution of 6C4 (200 mg, 0.76 mmol) in DCM (5 ml) was added triethylamine (0.09 g, 0.13 ml, 0.91 mmol) and allyl bromide (0.90 g, 0.65 ml, 7.61 mmol). The solution was allowed to stir at room temperature for 2 hours. The solvent was removed and the crude reaction mixture was passed through a plug of silica, eluting with petroleum ether:ethyl acetate (8:2) to yield 6C7 as a yellow oil (0.80 g, % yield).

1H NMR (CDCl$_3$, 300 MHz) δ$_H$ 2.58 (1H, dd, J=6.7 Hz & 18.8 Hz, CH of CHC$\underline{H}_2$CO), 2.68 (1H, dd, J=4.2 Hz & 18.8 Hz, CH of CHC$\underline{H}_2$CO), 2.9–3.09 (6H, m, 3×C$\underline{H}_2$), 3.72–3.82 (1H, quin, J=7.6 Hz, C$\underline{H}$CH$_2$), 4.67 (1H dd, J=6.7 Hz & 4.2 Hz, C$\underline{H}$CH$_2$CO), 5.05 & 5.08 (2H, 2×dd, J=10.2 Hz & 1.8 Hz & 1.3 Hz, CH$_2$CH=C$\underline{H}_2$), 5.80 (1H, m, CH$_2$C$\underline{H}$CH$_2$), 7.11–7.21 (4H, m, 4×Ar—$\underline{H}$), 7.42 (1H dt, J=7.8 Hz, 1×Ar—$\underline{H}$), 7.64 (1H, dt, J=7.7 Hz & 1.2 Hz 1×Ar—$\underline{H}$), 7.74 (2H, dt, J=7.6 Hz, 2×Ar—$\underline{H}$).

$^{13}$C NMR (CDCl$_3$, 75.47 MHz) δ$_C$ 36.0, 38.7, 39.2, 50.2, 116.3 (5×$\underline{C}$H$_2$), 57.4, 61.0 (2×$\underline{C}$H), 122.9, 124.2, 124.6, 126.3, 126.4, 128.5, 134.8, 137.2 (8×Ar—$\underline{C}$H), 126.4, 141.4, 141.6, 156.4 (4×Ar—$\underline{C}$), 204.7 ($\underline{C}$=O).

Synthesis of 6C8

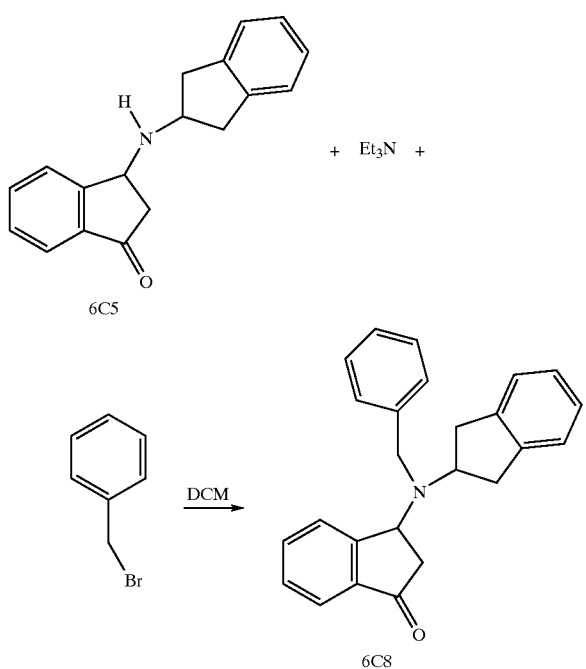

To a solution of dimer 6C4 (200 mg, 0.76 mmol) in DCM (5 ml) was added triethylamine (0.09 g, 0.13 ml, 0.91 mmol) and benzyl bromide (1.30 g, 0.90 ml, 7.61 mmol). The solution was allowed to stir at room temperature for 2 hours. The solvent was removed and the crude reaction mixture was passed through a plug of silica, eluting with petroleum ether:ethyl acetate (8:2) to yield 6C8 as a yellow oil (0.80 g, 30%).

$^1$H NMR (CDCl$_3$, 300 MHz) δ$_H$ 2.63 (1H, dd, J=7.0 Hz & 18.8 Hz, CH of CHCH$_2$CO), 2.81 (1H, dd, J=3.8 Hz & 18.8 Hz, CH of CHCH$_2$CO), 2.95–3.13 (4H, m, 2×CH$_2$), 3.58–3.71 (2H, m, CH$_2$Ph), 3.76 (1H t, J=7.6 Hz, CHCH$_2$CO), 4.65–4.68 (1H, m, CHCH$_2$), 7.14–7.48 (10H, m, 10×Ar—H), 7.67 (1H, dt, J=1.2 Hz, 7.68 Hz, 1×Ar—H), 7.76 (1H, d, J=7.7 Hz, 1×Ar—H), 7.87 (1H, d, J=7.7 Hz, 1×Ar—H).

$^{13}$C NMR (CDCl$_3$, 75.47 MHz) δ$_C$ 35.2, 38.6, 38.7, 50.9 (4×HH$_2$), 56.9, 60.4 (2×CH), 122.8, 124.0, 124.5, 126.2, 126.3, 126.8, 128.0, 128.2, 128.2, 128.4, 128.6, 128.8, 134.7 (13×Ar—CH), 137.1, 139.9, 141.2, 141.4, 156.1 (5×Ar—C), 204.5 (C=O).

Synthesis of 6C9

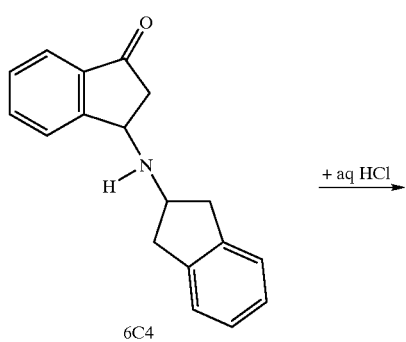

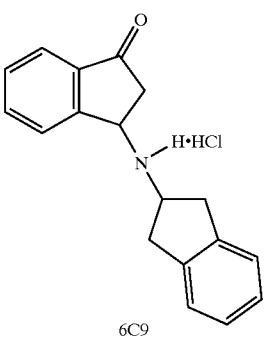

6C4 (100 mg, 0.38 mmol) was dissolved in methanol. To this was added a 2M aqueous HCl solution (5 ml), the flask was stirred vigorously and toluene was added to the flask and it was evaporated to dryness. The salt of this dimer was then extracted into water and evaporation of the water left 6C9 as a yellow solid. This was then partitioned between ethyl acetate and water. The aqueous layer was isolated and washed with ethyl acetate. Evaporation of the aqueous layer left the BRA 128 as a white solid, which was then recrystallised prom water and methanol to yield white crystals of 6C9 (84 mg, 72.4%).

$^1$H NMR (D$_2$O, 300 MHz) δ2.89 (2H, d, J=19.4 Hz, CHCH$_2$CO), 3.07 & 3.14 (1H, d, J=6.2 Hz, CH of CH$_2$CHCH$_2$), 3.18 & 3.26 (1H, d, J=5.5 Hz, CH of CHCHCH$_2$), 3.22 (1H, d, J=8.1 Hz, CH of CH$_2$CHCH$_2$), 3.31–3.42 (1H, q, J=8.1 Hz, CH of CH$_2$CHCH$_2$), 4.26 (1H, t, J=6.8 Hz, CH$_2$CHCH$_2$), 5.18 (1H, d, J=6.4 Hz, CHCH$_2$CO), 7.17 (2H, m, 2×Ar—H), 7.59 (1H, superimposed d, J=7.1 & 6.4 Hz, 1×Ar—H), 7.76 (1H, d, J=6.8 Hz, 1×Ar—H).

$^{13}$C NMR (D$_2$O, 75.47 MHz) δ$_C$ 38.4, 38.8, 42.6 (CH$_2$), 56.86 60.0 (CH), 127.2, 127.6, 127.7, 129.7, 130.2, 130.3, 134.1, 139.4 (8×Ar—CH), 141.5, 141.6, 142.0, 150.3 (4×Ar—C), 207.3 (C=O).

Synthesis of 6C10

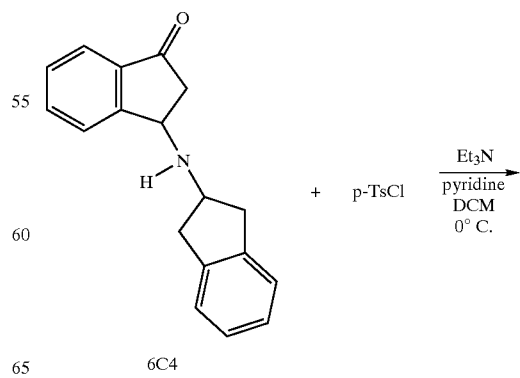

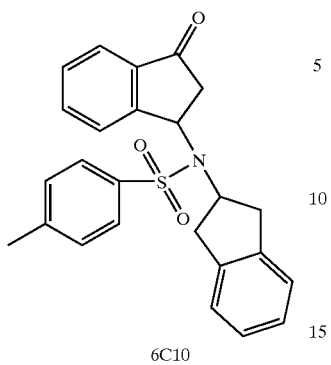

6C10

To a stirring solution of 6C4 (200 mg, 0.76 mmol) and p-toluenesulfonyl chloride (1.45 g, 7.60 mmol) in DCM (10 ml) was added triethylamine (0.09 g, 0.13 ml, 0.91 mmol). The solution was allowed to stir at 0° C. for 15 mins. The solution was allowed to stir at room temperature for a further hour then to this solution was added pyridine (0.26 ml) and the reaction was allowed to stir for a further 2 hours. The crude reaction mixture was passed through a flash silica column, eluting with petroleum ether:ethyl acetate 1:4. 6C10 was isolated as a yellow solid (284 mg, 89.3%).

$^{13}$C NMR (CDCl$_3$, 75.47 MHz) $\delta_C$ 21.2 (CH$_3$), 37.4, 37.4, 38.0 (3×CH$_2$), 54.8, 57.9 (CH), 123.1, 124.0, 124.2, 125.0, 125.6, 126.5, 126.9, 127.9, 128.7, 128.9, 129.5, 134.6 (12×Ar—CH), 136.9, 137.5, 138.2, 138.3, 139.7, 139.9, 143.3, 151.9, (6×Ar—C & 2×qC), 201.8 (C=O).

Synthesis of 6C11

To a solution of 6C4 (200 mg, 0.76 mmol) in DCM (5 ml) was added triethylamine (0.15 g, 0.20 ml, 1.48 mmol) and acetic anhydride (0.12 g, 0.11 ml, 1.17 mmol). To this stirring solution was added N,N-dimethylaminopyridine (0.10 g, 0.82 mmol). The reaction was allowed to stir at room temperature for 2 hours. Additional acetic anhydride (0.12 g, 0.11 ml, 1.17 mmol) was added and the reaction was allowed to stir at room temperature for 1 hour. The solvent was removed and the crude reaction mixture was passed through a plug of flash silica, eluting with petroleum ether: ethyl acetate, 4:1. 6C11 was isolated as a solid (110 mg, 47.5%).

$^1$H NMR (CDCl$_3$, 300 MHz) $\delta_H$ 2.09–5.50 (11H, br m, CH$_3$, CH$_2$'s and CH), 7.00–7.95 (8H, br. m, 8×Ar—H)

$^{13}$C NMR (CDCl$_3$, 75.47 MHz) $\delta_C$ 20.6, 20.9 (CH$_3$), 23.0, 23.8, 29.5, 35.8, 36., 38.0, 42.1, 42.3, 43.9 (3×CH$_2$), 52.3, 55.9, 57.0, 58.7, 60.2, (2×CH), 123.3, 123.8, 124.0, 124.2, 124.5, 124.6, 124.8, 125.3, 126.0, 127.2, 127.9, 129.5, 134.5, 135.4, 137.6, (Ar—CH), 139.6, 139.7, 141.1, 152.2, 154.3 (Ar—C) 170.1, 171.0 (CH$_3$CON), 201.5, 202.8 (CO)

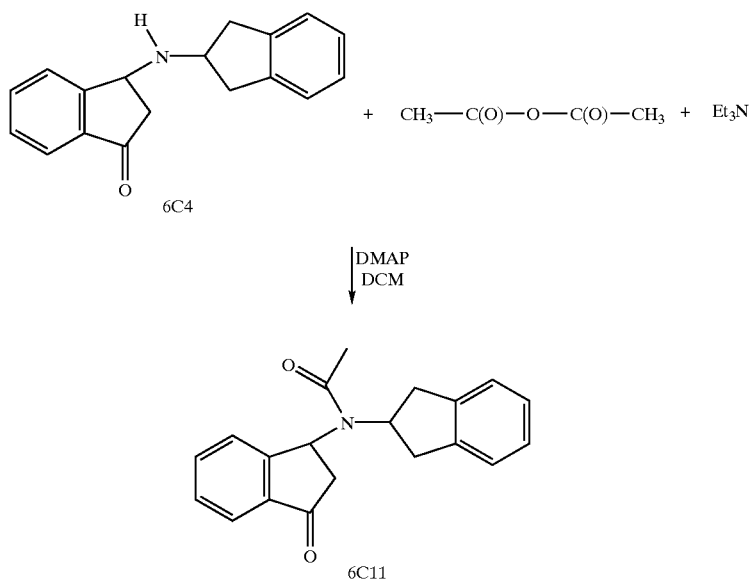

Synthesis of 6C12

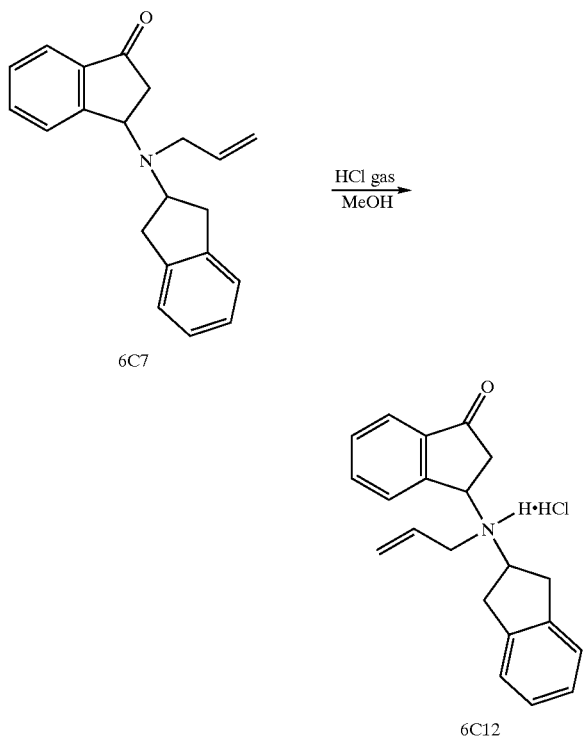

Compound 6C7 (100 mg) was dissolved in dry methanol (5 ml), dry HCl gas was bubbled through the solution for 5 mins. The methanol was then evaporated off and a white solid remained. The solid was then partioned between water and ether. The aqueous layers were combined and evaporated to dryness. The white solid 6C12 which remained was dried on the vac line (93%).

It will be appreciated that the compounds include pharmacologically acceptable salts, esters, isomers and solvates thereof. One example of a possible ester is a salicylate in at least one and possibly several suitable positions on the compound. This opens up the possibility of a combination therapy using an indane dimer and aspirin in a single molecule. The weight ratio of the base indane dimer to aspirin may be selected by providing a salicylate at a number of selected positions on the dimer.

It will be appreciated most of the compounds have one or more chiral centres and hence exist as a pair of enantiomers or as a mixture of diastereomers. This may have an effect on the pharmacological properties.

It will be appreciated that for pharmaceutical purposes the active compounds may be formulated in any desired form using any suitable excipients and/or carriers. For example, particularly in the case for use to achieve antiinflammatory activity the compound may be formulated in a pharmaceutical composition suitable for topical/transdermal application.

Pharmacology

Introduction

The indane dimers according to the invention have potent mast cell stabilising activity, smooth muscle relaxing activity, and anti-inflammatory activity. Such compounds are, therefore, potential anti-asthmatic agents with bronchodilator activity. The mast cell stabilising activity of the compounds suggests their potential use in the treatment of allergic rhinitis, allergic conjunctivitis and other anaphylactic or allergic conditions. The anti-inflammatory activity may have applications in gout, rheumatic diseases, ankylosing spondylitis, polymyalgia rheumatica, temporal arteritis, polyarteritis nodosa, polymyositis and systemic lupus arteriosis and other inflammatory conditions. Topical applications may include: atopic excema, weeping excemas psoriasis, chronic discoid lupus erythematosus, lichen simplex chronicus, hypertrophic lichen planus, paimar plantar pustulosis. They may also have potential in the treatment of some malignant diseases and as immunosuppressants.

The smooth muscle relaxing activity of the compounds may have potential in the treatment of hypertension and peripheral vascular disease, such as intermittent claudication and Reynaud's syndrome, as well as other cardiovascular disorders, such as congestive heart failure, angina pectoris, cerebral vascular disease and pulmonary hypertension. Such compounds are also indicated for potential use in the treatment of certain disorders of the gastrointestinal tract, such as diverticular disease and irritable bowel syndrome. Similarly, these compounds may have potential as agents for the treatment of disorders of the genito-urinary tract, such as premature labour, incontinence, renal colic and disorders associated with the passage of kidney stones. Members of this group of compounds may also have potential as diuretics, analgesics, antipyretics, local anaesthetics, central nervous system depressants and hypoalycaemic agents.

The compounds were assessed for their ability to stabilize mast cell membranes in vitro. Mast cells treated with the compounds and un-treated mast cells were stimulated to release histamine. A reduction in histamine release by the treated cells compared to the untreated cells indicates stabilisation of the membrane. The compounds were assessed for their ability to relax smooth muscle in vitro. Intestinal smooth muscle was stimulated to contract, using calcium chloride and subsequently treated with the compounds, relaxation of the contraction was measured for each compound. The effects of the compounds were also studied on relaxation of guinea-pig tracheal muscle. In the rat paw oedema test, the drugs were administered systemically prior to inducing inflammation by the injection of carageenan below the plantar aponeurosis of the hind paw. The volume of the paw was determined both before and after treatment as an index of oedema. In the mouse ear oedema test, the drugs were administered topically prior to inducing inflammation by the topical application of arachidonic acid. The width of the ear was determined both before and after treatment as an index of oedema.

There follows protocols of each of the assays used and a summary of the results.

| ABBREVIATIONS | |
|---|---|
| BSS | buffered salt solution |
| $CaCl_2$ | calcium chloride |
| $CO_2$ | carbon dioxide |
| DMSO | dimethyl sulphoxide |
| DSCG | disodium cromoglycate |
| $dH_2O$ | distilled water |
| HCl | hydrochloric acid |
| HEPES | N-2-hydroxyethylpiperazine-N-2-ethanesulphonic acid |
| KCl | potassium chloride |
| $l_{em}$ | emission wavelength |
| $l_{ex}$ | excitation wavelength |
| M | Molar |
| $MgCl_2$ | magnesium chloride |

| ABBREVIATIONS | |
|---|---|
| min | minutes |
| µl | microliters |
| mM | milli-molar |
| NaCl | sodium chloride |
| NaHCO$_3$ | sodium hydrogen carbonate |
| NaH$_2$PO | sodium hydrogen phosphate |
| NaOH | sodium hydroxide |
| O$_2$ | oxygen |
| oPT | o-phthaldialdehyde |
| S.E.M. | standard error of mean |
| w/v | weight per volume |
| v/v | volume per volume |

Methods
Histamine Release Assay

The buffered salt solution (BSS) was prepared in advance (NaCl 137 mM; KCl 2.7 mM; MgCl$_2$ 1.0 mM; CaCl$_2$ 0.5 mM, NaH$_2$PO$_4$ 0.4 mM; Glucose 5.6 mM; HEPES 10 mM). This was dispensed into test tubes and heated to 37° C., each test tube contained 4.5 ml BSS. The solvent blank was supplemented with 0.5% (v/v) dimethyl sulphoxide (DMSO) or 0.5% (v/v) distilled water (dH$_2$O). The two positive controls were supplemented with 0.5% (v/v) dH$_2$O/ 2×10$^{-5}$M disodium cromoglycate (DSCG) and 0.5% (v/v) DMSO/2×10$^{-5}$M DSCG. The test compounds' incubation tubes contained 2×10$^{-5}$M test compound/0.5% (v/v) DMSO. The basal release, maximum release and total histamine content incubation tubes contained no additions.

Female Wistar rats (200–300 g) were killed in an atmosphere of saturated CO$_2$. Pre-warmed BSS (10 ml) was injected i.p. and the abdomen was massaged for 3 min. The BSS, with suspended mast cells and other cells, was aspirated following a mid-line incision. The aspirate was centrifuged for 5 min at 400 g and the supernatant removed. The cells were re-suspended in BSS, at 4° C., and centrifuged as before the cells were washed in this manner a total of three times. Following the final wash, the pelleted cells were stored at 4° C., for use as soon as possible.

The cells were re-suspended in 7 ml BSS. From this, 0.5 ml aliquots were transferred to each of the incubation tubes. After 10 min at 37° C. with gentle agitation, Compound 48/80 was added to a final concentration of 2 mg/ml, in order to stimulate histamine release. The cell stimulation was stopped after 2 min by the addition of 0.5 ml ice cold BSS, the incubation tubes were transferred to an ice bath. The cell suspensions were centrifuged for 5 min at 400 g. The "total histamine content" tube was placed at 100° C. for 2 min prior to centrifugation. The supernatants were retained for histamine assay.

To 2 ml of supernatant from each tube was added 0.4 ml of 1M NaOH and 0.1 ml oPT (1% (w/v) in methanol). This was incubated at room temperature for 4 min. The reaction was stopped by the addition of 0.2 ml of 3M HCl. The supernatant from each incubation tube was assayed in duplicate and run simultaneously with a standard curve in the range 0–1000 ng/ml. The presence of the fluorescent product of the reaction was measured using a Shimazu RF-1501 spectrofluorophotometer set at $\lambda_{ex}$=360 nm, $\lambda_{em}$=450 nm.

Each drug was tested on at least five animals (n=5). The results were expressed as a percentage of maximum, compound 48/80 induced, histamine release in the solvent blank sample. Each drug was compared to DSCG on the same tissues. The basal histamine release in untreated cells was noted, expressed as a percentage of the total histamine content of the cells in suspension. The maximum histamine released by the cells in response to compound 48/80, in the relevant solvent blank sample, was expressed in the same manner. Overall, the mean basal release was 9.60% (S.E.M.=1.02) of total histamine content of the cells (n=55). The maximum stimulated histamine release was 67.38% (S.E.M.=2.90) in the present of 0.5% (v/v) dH$_2$O and 54.87% (S.E.M.=2.69) on the presence of 0.5% (v/v) DMSO of total histamine content of the cells (n=55).

Smooth Muscle Effects

Guinea pigs (350 g approx.), of either sex, were killed in an atmosphere of saturated CO$_2$. The abdomen was opened by a mid-line incision and the small intestine was removed. The trachea was removed and sectioned between the cartilage rings, which were then split through.

Segments of ileum (1–1.5 cm) were suspended in a high potassium, no calcium Krebs buffer (NaCl 160.44 mM); KCl 45 mM; MgCl$_2$ 0.54 mM; NaH$_2$PO$_4$ 0.89 mM; NaH$_2$CO$_3$ 24.9 mM; Glucose 11.1 mM). Tracheal sections were suspended in normal Krebs buffer (NaCl 236.5 mM; KCl 4.7 mM; CaCl$_2$ 2.5 mM; MgCl$_2$ 0.54 mM; NaH$_2$PO$_4$ 0.89 mM; NaHCO$_3$ 24.9 mM; Glucose 11.1 mM). The solutions were maintained at 37° C. by a jacketed organ bath and gassed with 95% O$_2$ and 5% CO$_2$. The tissues were anchored by thread to the bottom of the organ bath and suspended from force displacement transducers under a resting tension of 1 g approx. in the case of ileum and 4 g approx. in the case of trachea. Isotonic contractions were recorded using a MacLab/4e system in conjunction with the Chart 3.3.1 software package. Surplus tissue was stored at 4° C. in Krebs buffer, for a maximum of 48 hours.

Four segments of tissue were suspended and observed concurrently. Contractions were initiated by the addition of 25 µl of 1M CaCl$_2$ (a final concentration of 2.5 mM). The contractions stabilized with time, 10–15 min, and could be maintained for up to 45 min. from the addition of the CaCl$_2$. The tracheal sections were allowed to develop spontaneous resting tension over a period of 30 mins.

Stock solutions of drug were prepared at 10$^{-3}$M in 50% (v/v) DMSO. These were diluted to give; 10$^{-4}$M in 5% (v/v) DMSO and 10$^{-5}$M in 0.5% (v/v) DMSO. In cases of poor solubility the 10$^{-3}$M stock was made up in higher concentrations of DMSO. Solvent 'blank' solutions were prepared containing 50%, 5% and 0.5% (v/v) DMSO (or as appropriate). A cumulative dose-response assay was carried out in the range 5×10$^{-8}$M to 10$^{-5}$M. A second cumulative dose-response assay was carried out using DMSO 'blank' solutions only.

Each drug was tested, in duplicate, on at least three different animals (n=3). The results were expressed as percentage inhibition of the CaCl$_2$ induced contraction in the case of ideal tissue and percentage relaxation in the case of tracheal tissue, for each tissue, at each concentration of drug in DMSO. The effect of DMSO, for each tissue at each concentration, was subtracted from the effect of the drug in DMSO, to give the effect of the drug alone. A log dose vs. response curve was plotted for each drug using the mean and the standard error of the mean for the cumulated results.

In vivo Inflammation Models

The mouse ear oedema model was performed using Laca mice (25–35 g), of either sex. The animals were sedated with fentanyl/fluanisone (Hypnorm, Janssen). One ear was treated by the topical application of one of a range of test compounds, indomethacin or dexamethasone (all at 300 µg ear in acetone) drug. After 30 min, oedema was induced by the topical application of arachidonic acid (10 µl at 0.4 g/ml in acetone). The thickness of each ear was measured, both before and 60 min after the induction of oedema, using a micrometer screw gauge. Ear oedema was calculated by comparing the ear width before and after induction of oedema and expressed as percentage normal.

Results

Mast Cell Stabilisation and Smooth Muscle Relaxation

The findings of the hista mine release and the smooth muscle effect assays are summarised in the accompanying tables of results. The results from some of the compounds are illustrated in the accompanying graphs. The results indicate that these compounds show a wide variety of smooth muscle relaxing and mast cell stabilising activity, and that these two effects are not related (i.e. a good mast cell stabiliser is not necessarily a good smooth muscle relaxant and vice versa).

Results for Histamine Release Assay and Smooth Muscle

|  | Percentage Inhibition of: | | | | | | |
|---|---|---|---|---|---|---|---|
|  | CaCl2 Induced Contractions (±S.E.M.) | | | | | | Histamine Release (± S.E.M.) 2 × |
| Conc. (M) | $3 \times 10^{-8}$ | $10^{-7}$ | $3 \times 10^{-7}$ | $10^{-6}$ | $3 \times 10^{-6}$ | $10^{-5}$ | $10^{-5}$ |
| 5C3 | 0.53 ±0.38 | 2.61 ±0.77 | 3.78 ±1.80 | 7.21 ±2.02 | 15.05 ±2.90 | 29.99 ±2.92 | 32.77 ±7.24 |
| 5C4 | -0.86 ±0.40 | -0.86 ±0.68 | -0.99 ±1.28 | 1.15 ±1.38 | 5.08 ±1.60 | 19.14 ±1.80 | 5.68 ±2.21 |
| 5C5 | -0.26 ±0.27 | 0.28 ±0.44 | 0.43 ±0.54 | 1.56 ±1.16 | 3.56 ±1.00 | 10.50 ±1.54 | 58.68 ±2.47 |
| 5C6 | -1.00 ±0.89 | 0.02 ±0.90 | 0.36 ±0.69 | 1.31 ±1.59 | 8.84 ±0.91 | 20.94 ±0.80 | 77.77 ±1.94 |
| 5C7 | 0.16 ±0.24 | -0.44 ±0.50 | -0.36 ±0.88 | -1.72 ±0.69 | 0.00 ±1.25 | 2.06 ±1.75 | 24.12 ±4.41 |
| 6C4 | 2.16 ±0.65 | 3.02 ±1.10 | 4.63 ±1.11 | 8.84 ±1.77 | 17.11 ±2.03 | 33.46 ±2.43 | 14.92 ±8.55 |
| 6C6 | 0.15 ±0.37 | 2.75 ±1.92 | 4.64 ±2.60 | 9.01 ±3.48 | 12.62 ±3.55 | 22.95 ±4.32 | 68.05 ±6.96 |
| 6C7 | 1.16 ±1.66 | 3.15 ±1.57 | 4.52 ±1.60 | 5.36 ±1.89 | 10.67 ±1.61 | 21.83 ±3.74 | 89.46 ±1.84 |
| 6C8 | 1.97 ±1.58 | 2.94 ±1.62 | 3.26 ±1.37 | 4.69 ±1.35 | 11.29 ±1.33 | 31.14 ±3.18 | 88.59 ±0.61 |
| 6C9 | 0.31 ±0.33 | 0.61 ±0.54 | -1.76 ±0.72 | -2.94 ±1.06 | -0.86 ±0.89 | 1.58 ±2.01 | 43.60 ±7.11 |

|  | Percentage Inhibition of: | | | | | |
|---|---|---|---|---|---|---|
|  | CaCl2 Induced Contractions (±S.E.M.) | | Spontaneous Tone (±S.E.M.) | | | Histamine Release (±S.E.M.) |
| Conc. (M) | ileum $3 \times 10^{-6}$ | $10^{-5}$ | trachea $3 \times 10^{-6}$ | $10^{-5}$ | | $2 \times 10^{-5}$ |
| 5C3 TS |  |  |  |  |  | 46.02 ±4.65 |
| 5C3 TR | -0.50 ±0.93 | 4.59 ±2.03 | 1.58 ±1.34 | 2.78 ±1.15 |  | 45.30 ±2.42 |
| 5C3 BS |  |  |  |  |  | 67.47 ±3.65 |
| 5C3 BR | 1.39 ±0.99 | 10.71 ±1.67 | 0.44 ±1.55 | 0.09 ±1.88 |  | 52.20 ±3.35 |
| 5C6 TS | 5.29 ±2.16 | 19.41 ±4.22 | 1.63 ±0.93 | 2.71 ±1.39 |  | 75.15 ±5.42 |
| 5C6 TR |  |  | 1.50 ±1.05 | 4.97 ±1.03 |  | 79.98 ±3.19 |
| 5C6 BS | 13.66 ±6.91 | 31.47 ±9.12 | 2.03 ±1.37 | 4.09 ±1.51 |  | 80.29 ±3.81 |
| 5C6 BR | 8.72 ±2.02 | 31.64 ±3.38 |  |  |  | 78.84 ±3.99 |
| 5C8 |  |  |  |  |  | 14.33 ±2.47 |
| 5C9 | 9.06 ±3.90 | 18.31 ±3.80 | 2.64 ±2.59 | 2.38 ±1.72 |  | 14.33 ±2.47 |

| -continued | | | |
|---|---|---|---|
| 5C10 |  |  | 40.75 ±8.05 |
| 5C11 |  |  | 90.27 ±2.70 (n = 4) |
| 6C10 | -0.75 ±1.43 | 0.50 ±1.66 | 51.12 ±8.40 |
| 6C11 | 8.00 ±5.62 | 12.49 ±6.40 | 4.26 ±6.80 |
| 6C12 |  |  | 91.35 ±2.19 (n = 4) |

Inflammation Model
Mouse Ear Oedema

Responses of the mouse ear to single doses of a range of compounds compared to the response to indomethacin and dexamethasone, each at a dose of 300 μg per ear administered topically 30 min prior to administration of 400 μg of arachidonic acid. Values are expressed as the percentage increase in ear thickness 1 hour after administration of arachidonic acid (all n=4, solvent controls (n=8)). The results suggest that anti-inflammatory activity is not linked to mast cell stabilising activity.

| Compound | Mean % | SEM |
|---|---|---|
| Dexamethasone | 37.9 | 8.5 |
| Indomethacin | 39.6 | 5.8 |
| 6C7 | 71.5 | 15.7 |
| 6C6 | 73.0 | 8.7 |
| 5C6 | 52.0 | 20.3 |
| 6C11 | 26.0 | 6.3 |
| Solvent Control | 78.8 | 15.2 |

It will be appreciated that the compounds may have useful pharmacological properties other than those described above.

The invention is not limited to the embodiments hereinbefore described which may be varied in detail.

Appendix 1

| LIST OF ABBREVIATIONS USED | |
|---|---|
| AlCl$_3$ 835 | aluminium chloride |
| aq | aqueous |
| b.p. | boiling point |
| BrCH$_2$C$_6$H$_4$CO$_2$CH$_3$ | methyl 4-(bromomethyl)benzoate |
| BrCH$_2$CO$_2$CH$_3$ | bromomethyl acetate |
| BSS | buffered salt solution |
| CaCl$_2$ | calcium chloride |
| C$_2$H$_5$I | iodoethane |
| C$_6$H$_3$(CH$_3$)Br(CH$_3$) | bromo-m-xylene |
| C$_6$H$_5$CH$_2$Br | benzyl bromide |
| CDCl$_3$ | chloroform-d |
| CF$_3$SO$_3$Si(CH$_3$)$_3$ | trimethylsilyl trifluoromethanesulfonate (TMS triflate) |
| CH(OCH$_3$) | trimethylsilyl orthoformate |
| CH$_3$C$_6$H$_4$SO$_3$H.H$_2$O | p-toluenesulfonic |
| CH$_3$I | iodomethane |
| CLCH$_2$CH$_2$COCl | β-chloropropionylchloride |
| CO$_2$ | carbon dioxide |
| CS$_2$ | carbon disulfide |
| [(C$_6$H$_5$)$_3$P]$_3$RhCl | tris(triphenylphosphine)rhodium(1) chloride (wilkinsons catalyst) |
| [(CH$_3$)$_3$CO]$_3$Al | aluminium tri-tert-butoxide |
| DCM | dichloromethane |

LIST OF ABBREVIATIONS USED

| | |
|---|---|
| $dH_2O$ | distilled water |
| DMSO | dimethyl sulphoxide |
| DSCG | disodium cromoglycate |
| $Et_2O$ | ether |
| $Et_3N$ | triethylamine |
| EtOAc | ethyl acetate |
| EtOH | ethanol |
| $H_2C=CHCH_2Br$ | allyl bromide |
| $H_2NNH_2 \cdot H_2O$ | hydrazine hydrate.monohydrate |
| $H_2O$ | water |
| $H_2SO_4$ | sulphuric acid |
| HCl | hydrochloric acid |
| HEPES | N-2-hydroxyethylpiperazine-N-2-ethanesulphonic acid |
| $HOCH_2CH_2OH$ | ethylene glycol |
| IR | infra red |
| KCl | potassium chloride |
| LDA | lithium diisopropylamide |
| M | Molar |
| $MgCl_2$ | magnesium chloride |
| min | minutes |
| $\mu l$ | microliters |
| mM | milli-molar |
| m.p. | melting point |
| $N_2$ | nitrogen |
| $NaBH_4$ | sodium borohydride |
| NaCl | sodium chloride |
| $NaCN(BH_3)$ | sodium cyanoborohydride |
| $NaHCO_3$ | sodium hydrogen carbonate |
| $NaHCO_3$ | sodium bicarbonate |
| $NaH_2PO$ | sodium hydrogen phosphate |
| NaOH | sodium hydroxide |
| $Na_2SO_4$ | sodium sulphate |
| $NH_6Cl$ | ammonium chloride |
| NMR | nuclear magnetic resonance |
| $O_2$ | oxygen |
| oPT | o-phthaldialdehyde |
| Pd | palladium |
| RT | room temperature |
| $^tBuOH$ | tert butanol |
| $^tBuOK$ | potassium tert butoxide |
| S.E.M. | standard error of mean |
| THF | tetrahydrofuran |
| TLC | thin layer chromatography |
| $\mu l$ | microliters |
| Triflic Acid | trifluoromethanesulfonic acid |
| TMS Triflate | trimethyl silyl trifluoromethanesulfonate |
| v/v | volume per volume |
| w/v | weight per Volume |
| $ZnI_2$ | zinc iodide |
| $\lambda_{em}$ | emission wavelength |
| $\lambda_{2ex}$ | excitation wavelength |

Appendix 2

| | |
|---|---|
| 5C3 | 3-(N-1-indanylamino)-indan-1-one |
| 5C4 | 3-(N-1-indanylamino)indan-1-ol |
| 5C5 | 3-(N-methyl-N-1-indanylamino)-indan-1-one |
| 5C6 | 3-(N-prop-2-enyl-N-1-indanylamino)-indan-1-one |
| 5C7 | 3-(N-benzyl-N-1-indanylamino)-indan-1-one |
| 5C8 | 3-(N-1-indanylamino) -indan-1-one. Hydrochloride |
| 5C9 | N-1-Indanyl-N-3-indan-1-onylethanamide |
| 5C10 | N-1-Indanyl-N-3-indan-1-onyl-p-toluenesulfonamide |
| 5C11 | 3-(N-prop-2-enyl-N-1-indanylamino)-indan-1-one hydrochloride |
| 5C12 | 1-diindanyl ether |
| 6C4 | 3-(N-2-indanylamino)-indan-1-one |
| 6C5 | 3-(N-2-indanylamino)-indan-1-ol |
| 6C6 | 3-(N-methyl-N-2-indanylamino)-indan-1-one |
| 6C7 | 3-(N-prop-2-enyl-N-2-indanylamino)-indan-1-one |
| 6C8 | 3-(N-benzyl-N-2-indanylamino)-indan-1-one |
| 6C9 | 3-(N-2-indanylamino)indan-1-one. Hydrochloride |
| 6C10 | N-2-Indanyl-N-3-indan-1-onyl-p-toluenesulfonamide |
| 6C11 | N-2-Indanyl-N-3-indan-1-onylethanamide |
| 6C12 | 3-(N-prop-2-enyl-N-2-indanylamino)-indan-1-one hydrochloride |

What is claimed is:

1. A compound of Formula 5:

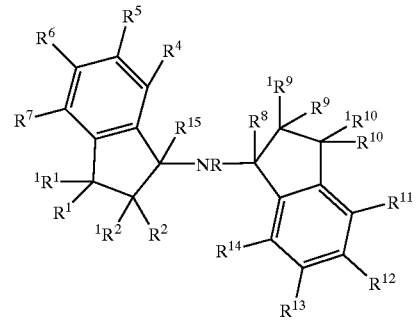

5 wherein

R is H, acyl, alkyl, allyl or benzyl group $R^2$, $^1R^2$, $R^4$ to $R^8$, $R^9$, $^1R^9$, $R^{10}$, $^1R^{10}$, $R^{11}$ to $R^{15}$ are each independently selected from the group consisting of:

H, halo, hydroxy, alkoxy, aryloxy, acetoxy, carboxy, alkyl carbonyl, hydro carbonyl, amino, amido, alkylamino, hydroxylamino, a sulfonic acid group, a sulfoxide group, a sulfone group, optionally substituted $C_1$–$C_{10}$ alkyl and optionally substituted $C_3$–$C_8$ cycloalkyl;

wherein any one or more of $R^2$, $^1R^2$; $R^9$, $^1R^9$; and $R^{10}$, $^1R^{10}$ may together optionally represent oxo, and wherein $R^1$ and $^1R^1$ are =O or when one of $R^1$ and $^1R^1$ is H then the other is OH.

2. A compound as claimed in claim 1 wherein the alkyl or cycloalkyl are substituted with one or more of the same or different of:

halo, oxo, hydroxy, alkoxy, aryloxy, acetoxy, carboxy, carbonyl, amino, amido, alkylamino, hydroxylamino.

3. A compound as claimed in claim 1 wherein each of $R^4$ to $R^7$ is hydrogen.

4. A compound as claimed in claim 1 wherein each of $R^{11}$ to $R^{14}$ is hydrogen.

5. A compound as claimed in claim 1 wherein the R group in NR represents hydrogen, acyl, alkyl, allyl or a benzyl group.

6. A compound as claimed in claim 1 wherein the R group in NR represents acyl.

7. A compound as claimed in claim 1 wherein the R group in NR represents alkyl.

8. A compound of Formula 6: wherein

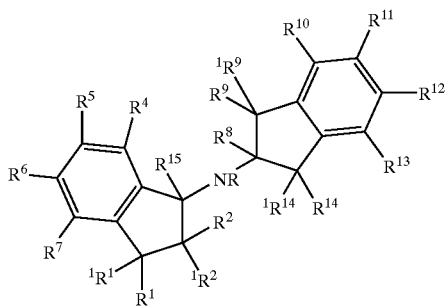

R is H, acyl, alkyl, allyl, benzyl or a sulfonate group
$R^1$, $^1R^1$, $R^2$, $^1R^2$, $R^4$ to $R^8$, $R^9$, $^1R^9$, $R^{10}$ to $R^{13}$, $R^{14}$, $^1R^{14}$ and $R^{15}$ are each independently selected from the group consisting of:
    H, halo, hydroxy, alkoxy, aryloxy, acetoxy, carboxy, alkyl carbonyl, hydro carbonyl, amino, amido, alkylamino, hydroxylamino, a sulfonic acid group, a sulfoxide group, a sulfone group, optionally substituted $C_1$–$C_{10}$ alkyl and optionally substituted $C_3$–$C_8$ cycloalkyl;
wherein any one or more of $R^1$, $^1R^1$; $R^2$, $^1R^2$; $R^9$, $^1R^9$; and $R^{14}$, $^1R^{14}$ may together optionally represent oxo.

9. A compound as claimed in claim 8 wherein the alkyl or cycloalkyl is substituted with one or more of the same or different of:
    halo, oxo, hydroxy, alkoxy, aryloxy, acetoxy, carboxy, carbonyl, amino, amido, alkylamino, hydroxylamino.

10. A compound as claimed in claim 8 wherein each of $R^4$ to $R^7$ is hydrogen.

11. A compound as claimed in claim 8 wherein each of $R^{10}$ to $R^{13}$ is hydrogen.

12. A compound as claimed in claim 8 wherein the R group in NR represents hydrogen, acyl, alkyl, allyl, benzyl or a sulfonate group.

13. A compound as claimed in claim 8 wherein the R group in NR represents acyl.

14. A compound as claimed in claim 8 wherein the R group in NR represents alkyl or a sulfonate group.

15. A pharmaceutical composition comprising a compound as defined in claim 1 and a pharmaceutically acceptable carrier.

16. A pharmaceutical composition comprising a compound as defined in claim 8 and a pharmaceutically acceptable carrier.

17. A compound selected from the group consisting of:

3-(N-1-indanylamino)-indan-1-one,
3-(N-1-indanylamino)indan-1-ol,
3-(N-methyl-N-1-indanylamino)-indan-1-one,
3-(N-prop-2-enyl-N-1-indanylamino)-indan-1-one,
3-(N-benzyl-N-1-indanylamino)-indan-1-one,
3-(N-1-indanylamino)-indan-1-one hydrochloride,
N-1-indanyl-N-3-indan-1-onylethanamide,
3-(N-prop-2-enyl-N-1-indanylamino)-indan-1-one, hydrochloride,
3-(N-2-indanylamino)-indan-1-one,
3-(N-2-indanylamino)-indan-1-ol,
3-(N-methyl-N-2-indanylamino)-indan-1-one,
3-(N-prop-2-enyl-N-2-indanylamino)-indan-1-one,
3-(N-benzyl-N-2-indanylamino)-indan-1-one,
3-(N-2-indanylamino)-indan-1-one hydrochloride,
N-2-indanyl-N-3-indan-1-onyl-p-toluenesulfonamide,
N-2-indanyl-N-3-indan-1-onylethanamide, and
3-(N-prop-2-enyl-N-2-indanylamino)-indan-1-one hydrochloride.

18. A pharmaceutical composition comprising a compound as defined in claim 17 and a pharmaceutically acceptable carrier.

19. A method of prophylaxis or treatment to achieve smooth muscle relaxing activity and/or mast cell stabilising activity and/or anti-inflammatory activity, which comprises administering an effective amount of a compound as defined in claim 1 to a subject in need of such therapy.

20. A method of prophylaxis or treatment to achieve smooth muscle relaxing activity and/or mast cell stabilising activity and/or anti-inflammatory activity, which comprises administering an effective amount of a compound as defined in claim 8 to a subject in need of such therapy.

* * * * *